United States Patent
Goto et al.

(10) Patent No.: US 8,139,829 B2
(45) Date of Patent: Mar. 20, 2012

(54) DIAGNOSTIC IMAGING SUPPORT SYSTEM AND DIAGNOSTIC IMAGING SUPPORT PROGRAM

(75) Inventors: Yoshihiro Goto, Tokyo (JP); Toru Nakagawa, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 999 days.

(21) Appl. No.: 11/883,902

(22) PCT Filed: Feb. 7, 2006

(86) PCT No.: PCT/JP2006/302053
§ 371 (c)(1),
(2), (4) Date: Apr. 25, 2008

(87) PCT Pub. No.: WO2006/085525
PCT Pub. Date: Aug. 17, 2006

(65) Prior Publication Data
US 2008/0292155 A1  Nov. 27, 2008

(30) Foreign Application Priority Data

Feb. 9, 2005 (JP) .................................. 2005-032604
Feb. 9, 2005 (JP) .................................. 2005-032605

(51) Int. Cl.
*G06K 9/00* (2006.01)
(52) U.S. Cl. ....................................... 382/128; 382/132
(58) Field of Classification Search .................. 382/128, 382/132, 172, 190
See application file for complete search history.

(56) References Cited

U.S. PATENT DOCUMENTS

| 4,903,203 | A * | 2/1990 | Yamashita et al. ............ 382/132 |
| 4,922,915 | A * | 5/1990 | Arnold et al. ................. 382/128 |
| 5,530,092 | A | 6/1996 | Meijer et al. |
| 5,835,619 | A | 11/1998 | Morimoto et al. |
| 6,411,729 | B1 * | 6/2002 | Grunkin ......................... 382/132 |
| 6,560,474 | B2 * | 5/2003 | Lee et al. ...................... 600/408 |
| 6,839,457 | B1 | 1/2005 | Azuma et al. |
| 6,892,088 | B2 | 5/2005 | Faulkner et al. |
| 7,539,332 | B1 * | 5/2009 | Al-Dayeh et al. ............ 382/128 |
| 2004/0068166 | A1 | 4/2004 | Faulkner et al. |

FOREIGN PATENT DOCUMENTS

| JP | 9-294740 | 11/1997 |
| JP | 9-511418 | 11/1997 |
| JP | 10-509075 | 9/1998 |
| JP | 11-155852 | 6/1999 |
| JP | 2000-126168 | 5/2000 |
| JP | 2004-105739 | 4/2004 |
| WO | WO00/74567 A1 | 12/2000 |

* cited by examiner

*Primary Examiner* — Louis Arana
(74) *Attorney, Agent, or Firm* — Cooper & Dunham LLP

(57) ABSTRACT

A diagnostic imaging support system includes input means (15) for setting a characteristic quantity for performing a predetermined threshold processing for a bone region in an image of a subject; control means (10) for reading out the image from storage means (11) which stores the image of the subject, extracting a diagnostic region including the bone region from the read image on the basis of the characteristic quantity set by the input means, and calculating, for the extracted diagnostic region, structure analysis information of the bone by use of component identification information representing a bone portion component and a component other than the bone portion; and display means (14) for displaying the calculated structure analysis information of the bone while relating it to the image of the subject.

15 Claims, 27 Drawing Sheets

(A)

(B)

(A)

(B)

(A)

801
SLICE POSITION (B)

802
SLICE IMAGE

*1:OTHER CHARACTERISTIC QUANTITIES (a)

(b)

(c)

(n)

(a)

(b)

(c)

(n)

DIAGNOSTIC IMAGING SUPPORT SYSTEM AND DIAGNOSTIC IMAGING SUPPORT PROGRAM

TECHNICAL FIELD

The present invention relates to a diagnostic imaging support system and a diagnostic imaging support program for obtaining, through image processing of medical images, information on progress of osteoporosis or the like.

The present application is a U.S. National Phase Application of PCT International Application PCT/JP2006/302053 filed on Feb. 7, 2006, which claims priority from Japanese Patent Nos. 2005-032604 and 2005-032605 duly filed under the Japanese Patent Law on Feb. 9, 2005 and Feb. 9, 2005, respectively, the entire contents of each of said applications are incorporated herein by reference.

BACKGROUND ART

In recent years, onset of osteoporosis in late middle age has been considered a problem. Especially, it has been known that bone density in women decreases greatly after menopause, because, due to a change in the hormone balance after the menopause, bone destruction through metabolism becomes predominant over bone production. As compared with men of the same age, women are more likely to suffer osteoporosis.

Further, recently, juvenile girls tend to suffer a condition so-called "preliminary climacteric disturbance," and we are in a situation where not only people of late middle age but also people of younger age may suffer osteoporosis.

Therefore, people in a wide range of ages desire establishment of techniques for assisting diagnostic imaging, diagnostic forecasting, and treatment plans for osteoporosis.

In view of the above, there has been proposed a method of measuring the bone density of a cancellous bone in diagnosis of osteoporosis performed by use of a medical diagnostic imaging apparatus such as an X-ray CT apparatus. In this measurement method, an average of CT values is used as an index for diagnosing osteoporosis, and is compared with results obtained from a plurality of bone density measurement phantoms so as to indirectly measure bone density (see, for example, Patent Document 1).

Patent Document 1: Japanese Patent Application Laid-Open (kokai) No. Heisei 11-155852

However, in the aforementioned conventional technique, since the internal structure of bones is not analyzed, an index for diagnosing, for example, the progress of osteoporosis cannot be accurately measured.

SUMMARY

In an aspect of this disclosure, there is provided a diagnostic imaging support system which can assist diagnostic imaging by use of information obtained through analysis of bone structure.

In another aspect, there is provided a diagnostic imaging support system comprises input means for setting a characteristic quantity for performing a predetermined threshold processing for a bone region in an image of a subject; control means for reading out the image from storage means which stores the image of the subject, extracting a diagnostic region including the bone region from the read image on the basis of the characteristic quantity set by the input means, and calculating, for the extracted diagnostic region, structure analysis information of the bone by use of component identification information representing a bone portion component and a component other than the bone portion; and display means for displaying the calculated structure analysis information of the bone while relating it to the image of the subject.

In another aspect, there is provided a diagnostic imaging support program that causes a computer to execute an input step of setting a characteristic quantity for performing a predetermined threshold processing for a bone region in an image of a subject; a step of extracting a diagnostic region including the bone region from the image of the subject on the basis of the characteristic quantity set by the input step; a step of calculating, for the extracted diagnostic region, structure analysis information of the bone by use of component identification information representing a bone portion component and a component other than the bone portion; and a step of displaying the calculated structure analysis information of the bone while relating it to the image of the subject.

Thus, diagnostic imaging assistance can be performed by use of the structure analysis information of a bone.

DESCRIPTION OF REFERENCE NUMERALS

| | |
|---|---|
| 10 | central processing unit (CPU) |
| 11 | main memory |
| 12 | magnetic disk |
| 13 | display memory |
| 14 | CRT display |
| 15 | mouse |
| 16 | controller |
| 17 | keyboard |
| 18 | speaker |
| 19 | common bus |
| 1a | communication network |
| 1b | other computers and CT apparatus |

BEST MODE FOR CARRYING OUT THE INVENTION

A preferred embodiment of a diagnostic imaging support system according to the present invention will next be described with reference to the attached drawings.

Figure 1:
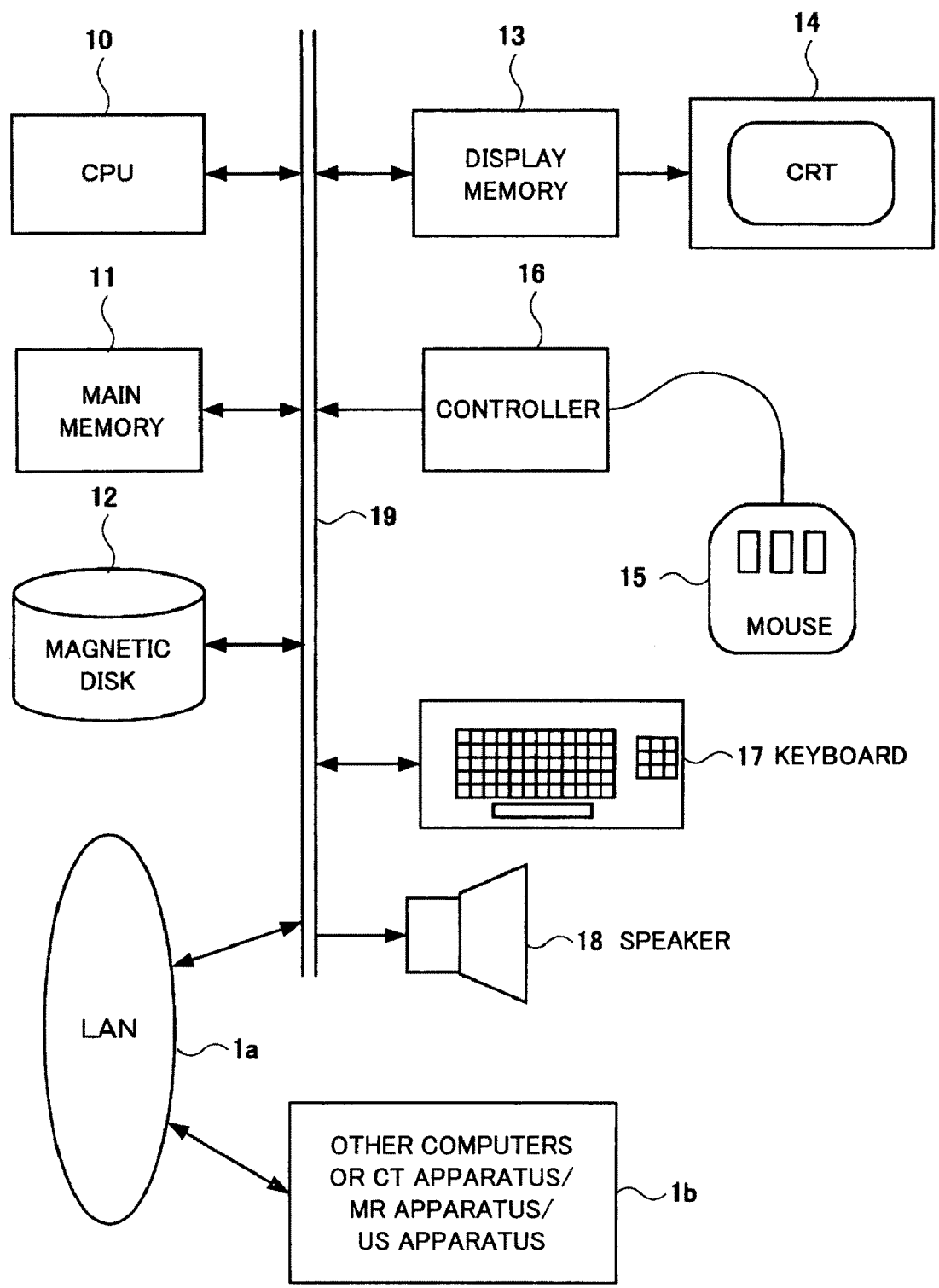
FIG. 1 Block diagram showing the overall hardware configuration of a diagnostic imaging support system to which the present invention is applied.

FIG. 1 is a block diagram showing the overall hardware configuration of a diagnostic imaging support system to which the present invention is applied. This diagnostic imaging support system quantifies and displays the structure of the trabecula of the spine on the basis of a plurality of tomograms (CT images or the like) collected for a region of interest by use of, for example, an X-ray CT apparatus.

The diagnostic imaging support system includes a central processing unit (CPU) 10 which controls operations of various constituent elements; a main memory 11 which stores a control program for the CPU; a magnetic disk 12 which stores a plurality of tomogram data sets, programs, and the like; a display memory 13 which temporarily stores image data for display; a CRT display 14 which serves as a display unit for displaying images on the basis of image data from the display memory 13; a mouse 15 and its controller 16 for operating switches created on the screen by means of software; a keyboard 17 having keys and switches for setting various parameters; a speaker 18; and a common bus 19 which connects the above-described constituent elements.

In the present embodiment, only the magnetic disk 12 is connected as a storage apparatus other than the main memory 11. However, a floppy disk drive, a hard disk drive, a CD-ROM drive, a magneto-optical disk (MO) drive, a ZIP drive, a PD drive, a DVD drive, a USB memory, or the like may also be connected. Moreover, the present system may be connected to various communication networks 1a, such as LAN (local area network), the internet, or a telephone line, via an unillustrated communication interface. In this case, the system can transmit image data to, and/or receive image data from, another computer or a CT apparatus/MR apparatus/US apparatus 1b. Transmission and reception of image data may be performed by connecting a medical diagnostic imaging apparatus capable of collecting tomograms of a subject, such as an X-ray CT apparatus, an MRI apparatus, or an ultrasonic diagnostic apparatus, to the above-described communication networks 1a, such as a LAN.

Figure 2:
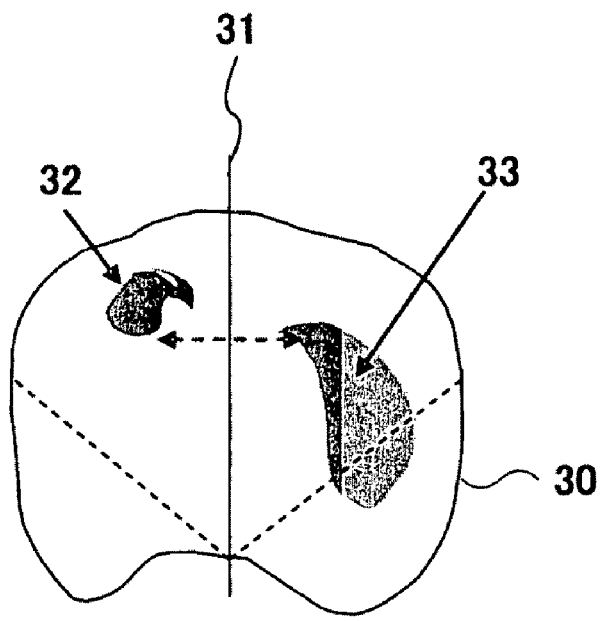
FIG. 2 Illustrations showing an example case where the degree of progress of osteoporosis is measured by making use of bilateral asymmetry of spine cancellous bone.
Figure 2:
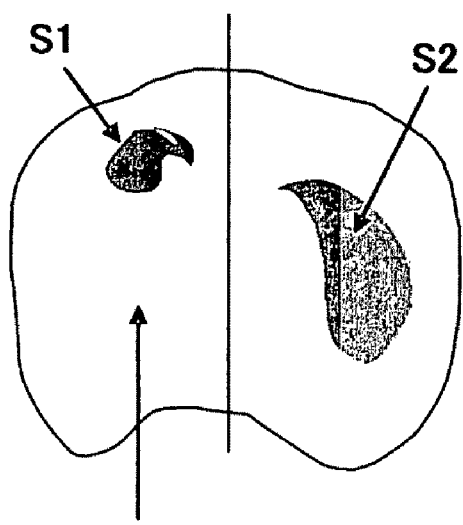
Figure 3:
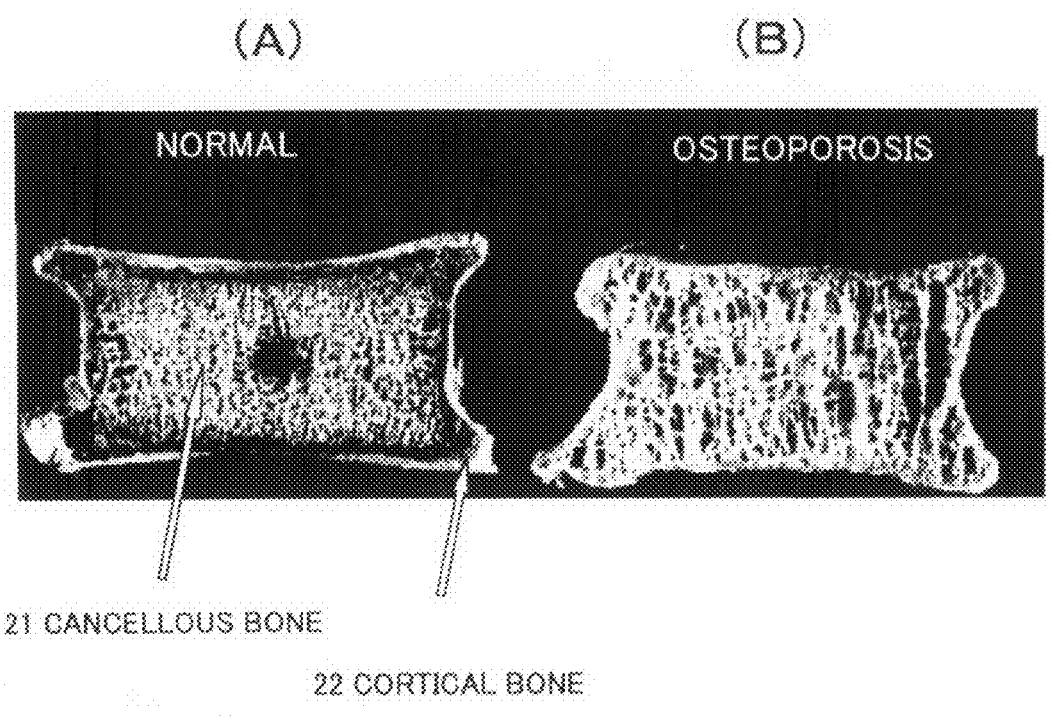
FIG. 3 Illustration showing example CT images of a healthy spine and a spine suffering osteoporosis.

First, there will be described a case where the structure of a trabecula is quantified and displayed. FIG. 2 is a pair of illustrations showing an example case where the structure of a trabecula is quantified and displayed by making use of bilateral asymmetry of the shape of the spine cancellous bone when it is divided to line-symmetric left and right portions. FIG. 3 is an illustration showing example CT images of a healthy spine and a spine suffering osteoporosis. FIG. 3(A) shows the cancellous bone 21 and cortical bone 22 of a healthy spine, and FIG. 3(B) shows those of a spine suffering osteoporosis. A main symptom of osteoporosis at an initial stage as shown in FIG. 3(B) is pain at the lumbar and back portions. After that, micro fracture of the spine bone is repeated, the spine bone collapses, the spine is gradually curved, and the height decreases. In a person suffering osteoporosis, the density distribution of the spine cancellous bone is observed to be asymmetrical in the left-right direction, and the spine bone is destroyed. In view of this, it is possible to measure the degree of asymmetry of the density distribution, and quantify and measure the structure of the trabecula by using the degree of asymmetry as the degree of progress of osteoporosis.

First, as shown in FIGS. 2(A) and 2(B), a cancellous bone 30 is symmetrically divided by a center line 31 into a left-hand region 32 and a right-hand region 33. For the left-hand region 32, the area S1 of a region where the following relation is satisfied is obtained.

$CT$ value of the right-hand region $-CT$ value of the left-hand region $>$ a threshold value Similarly, for the right-hand region 33, the area S2 of a region where the following relation is satisfied is obtained.

$CT$ value of the left-hand region $-CT$ value of the right-hand region $>$ a threshold value Here, the CT value is a specific example of a value representing the density of an image. When an image other than an X-ray CT image is used, the value denotes the density of the image.

The thus-obtained areas S1 and S2 are substituted in the following equation so as to obtain the value of a variable δ.

δ=abs(the standard CT value of a bone portion–the average CT value of the region excluding S1 and S2)

Here, abs means absolute value. The following judgment is rendered on the basis of the thus obtained value of the variable δ, and the degree of progress of osteoporosis is calculated.

```
if (δ < constant value){
    degree of progress of osteoporosis= constant × (S1+S2)/S
}else{
        measurement is impossible
}
``` where S represents the total area of the cancellous bone 30.

With this, the degree of progress of osteoporosis of the spine can be calculated by making use of a general low-radiation-dose CT image. That is, the structure of the terabecula can be quantified.

As shown in FIG. 2, the degree of progress of osteoporosis is defined on the basis of the bilateral asymmetry of the density distribution of the spine cancellous bone. In order to determine the degree of progress of osteoporosis more accurately, as shown in FIG. 3, the area or volume of hollow portions of a bone destroyed by osteoporosis is reflected on an index representing the degree of progress of osteoporosis. Since the hollow portions of a bone differ in shape and size, a value representing the size of the hollow portions is calculated from data regarding regions whose densities are lower than the average density of a predetermined bone region in a tomogram, and is used as a characteristic quantity which determines the degree of progress of osteoporosis.

Thus, the size of the hollow portions can be used as an index for predicting a disorder of a subject such as bone fracture, whereby more specific diagnostic support can be provided.

In the following description, a threshold processing or an area expanding method is used so as to determine the area or volume of hollow portions of a destroyed bone.

Figure 4:
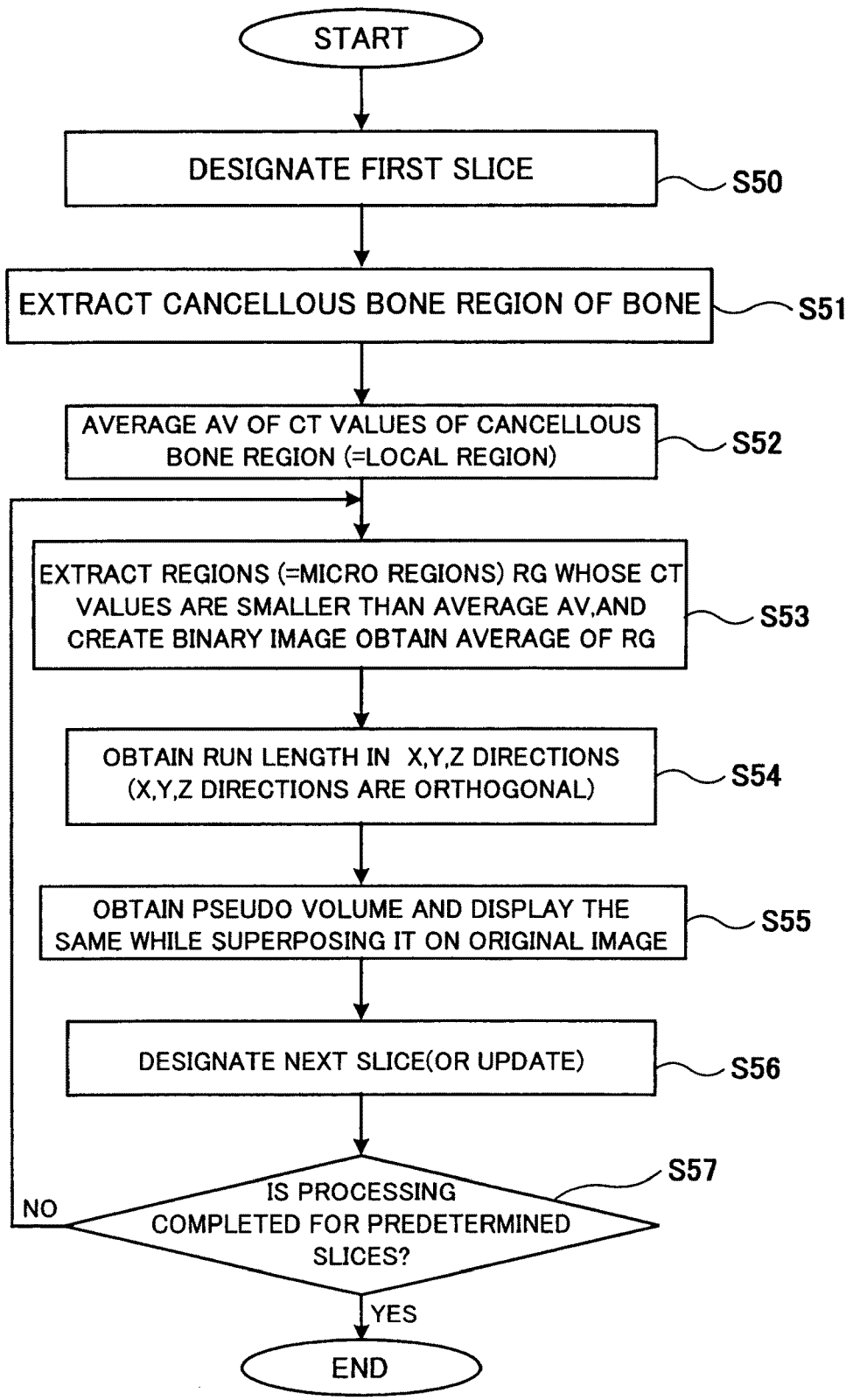
FIG. 4 Flowchart showing an example process for extracting the area or volume of cavities of a destroyed bone.
Figure 5:
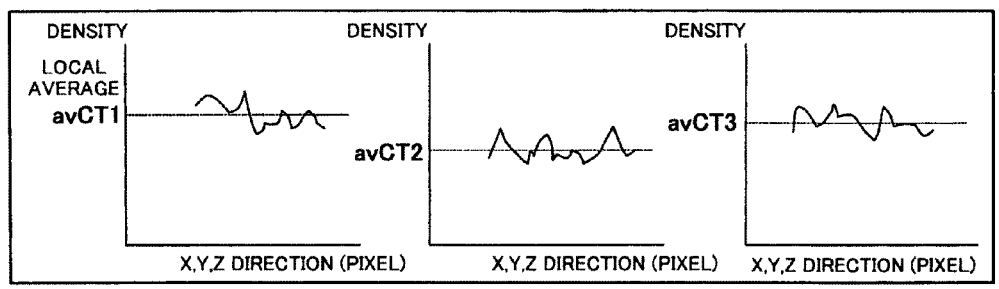
FIG. 5 Explanatory diagrams used for explaining a case where the process of FIG. 4 is performed by use of a run length method.
Figure 5:
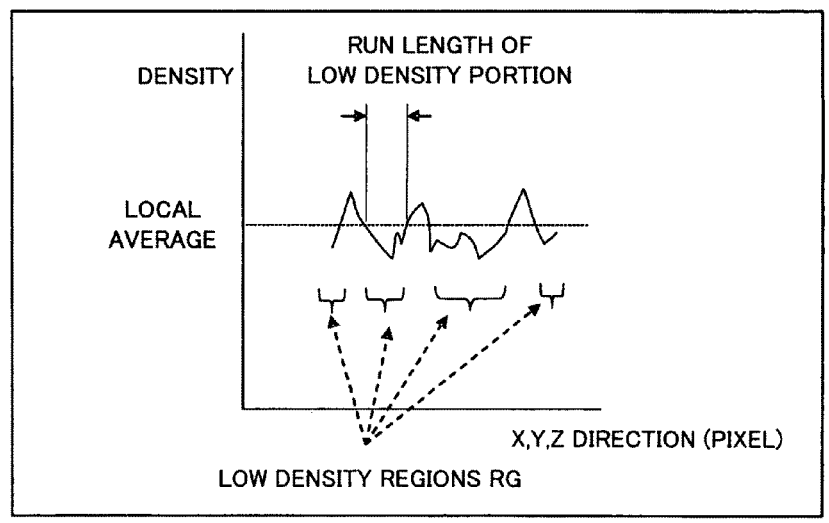

FIG. 4 is a flowchart showing an example process for extracting the area or volume of hollow portions of a destroyed bone. FIG. 5 is an explanatory diagram used for explaining a case where the process of FIG. 4 is performed by use of a run length method.

First, in step S50, after displaying a plurality of tomograms of a subject on a screen, by use of the mouse 15 or the like, an operator selects a tomogram corresponding to a first slice from the displayed tomograms, and sets a characteristic quantity to be used for threshold processing of the tomogram. The characteristic quantity may be set by selecting one of recommended values displayed on the screen in a menu form, or actually inputting the asymmetry or run lengths of the left and right regions of a cancellous bone region by use of the keyboard 17. No particular limitation is imposed on the means for inputting the characteristic quantity, so long as the operator can input the characteristic quantity. In step S51, for the first slice designated by the mouse, the CPU 10 extracts the cancellous bone region of the bone through, for example, threshold processing performed on the basis of the characteristic quantity. By the processing of this step, the region of the cancellous bone 30 is extracted as shown in FIG. 2.

In step S52, the CPU 10 obtains a local average avCT of CT values for each slice within the extracted cancellous bone. FIG. 5(A) shows local averages avCT1, avCT2, and avCT3 obtained in this manner. In the illustrated example, in order to facilitate understanding, the local averages are shown in the form of a graph in which the horizontal axis represents the pixel position on the image in the X, Y, Z direction, and the vertical axis represents the density (e.g., CT value) of a cross section of a cancellous bone portion.

In step S53, the CPU 10 extracts regions (low density regions/low density run lengths) RG where CT values are smaller than the local average avCT1, avCT2, or avCT3, creates binary images corresponding to the regions RG, and obtains the average CT value of the regions RG. FIG. 5(B) shows an example case where four low density regions (low density run lengths) RG are extracted. As in the case of FIG. 5(A), in order to facilitate understanding, FIG. 5(B) is shown in the form of a graph in which the horizontal axis represents the pixel position on the image in the X, Y, Z direction, and the vertical axis represents the density (e.g., CT value) of a cross section of the cancellous bone portion.

In step S54, the CPU 10 obtains the average of the low density run lengths RG in the X, Y, and Z directions, which are perpendicular to one another, in the binary image RG.

In step S55, the CPU 10 obtains a pseudo volume from the obtained average of the low density run lengths RG, and displays the pseudo volume, while superposing it on the original image.

In step S56, the operator designates the next slice on the screen or the CPU 10 updates the current slice with a previously set next slice.

In step S57, the CPU 10 determines whether or not the process is completed for predetermined slices. If the CPU 10 makes a "yes" determination (the process is completed), the CPU 10 ends the processing. If the CPU 10 makes a "no" determination, the CPU 10 again performs step S53.

Notably, in the threshold processing from steps S52 to S55, the following characteristic quantities 1 to 11 may be used.

Characteristic quantity 1: the values of 2D run lengths (RG)

Characteristic quantity 2: the average of 2D RG

Characteristic quantity 3: the local average of density–the density average of a micro region RG Characteristic quantity 4: the product of the total sum of RG regions and the average CT value of a micro region Characteristic quantity 5: the product of the average area of a micro region RG and the average of CT values of a small region Characteristic quantity 6: the product of the average 2D RG and the average CT value of a micro region when the total sum of micro regions is obtained Characteristic quantity 7: the product of ACT and the average within a local region of the average 2D RG of a micro region Characteristic quantity 8: the variance or standard deviation of density of a local region Characteristic quantity 9: the standard deviation of density of a local region×f(RG)

Characteristic quantity 10: the density expected value of a local region

Characteristic quantity 11: the quotient obtained from the density expected value of a local region and the product of ΔCT and the average within the local region of the average 2D RG of a micro region Notably, in the above-described calculation of the characteristic quantity, processing is performed by use of the original CT image. However, the processing may be performed for an image having undergone high-pass filter processing. Here, the average area is called "average 2D run length," and obtained from the product of the average of X-direction run lengths and the average of Y-direction run lengths (the X direction and the Y direction are orthogonal). The 2D run length is the product of run lengths of orthogonal two directions.

Figure 6:
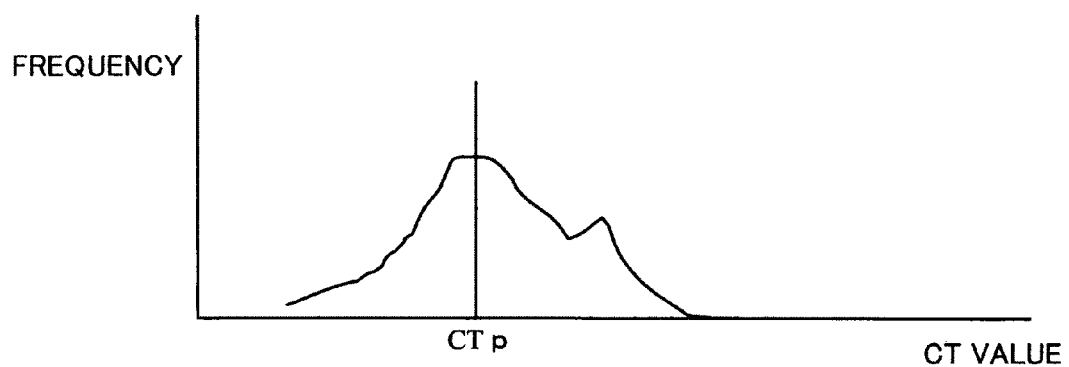
FIG. 6 Diagram showing a case where a peak position CTp of distribution (distribution of the cancellous bone) at which a histogram has a lower CT value (characteristic quantity) than those at other peak positions is used as a statistic quantity.

FIG. 6 is a diagram showing a case where a peak position CTp of distribution (distribution of the cancellous bone) at which a histogram has a lower CT value (characteristic quantity) than those at other peak positions is used as a statistic quantity. In the illustrated example, in order to facilitate understanding, the histogram is shown in the form of a graph where the horizontal axis represents CT value, and the vertical axis represents the frequency of occurrence of each CT value.

Since the frequency of occurrence of each CT value is shown in the form of a histogram, in some cases two or more peaks may appear. Therefore, of the plurality of peak positions, a peak position having a lower CT value is selected as a peak position Ctp of the cancellous bone.

Figure 7:
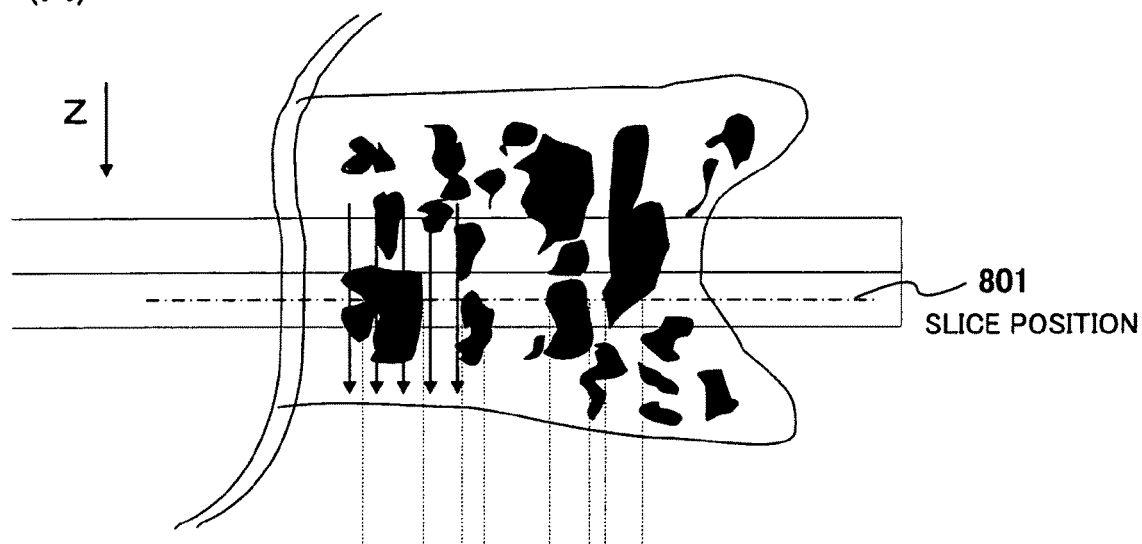
FIG. 7 Illustrations schematically showing the hollow portions of the bone shown in FIG. 3.
Figure 7:
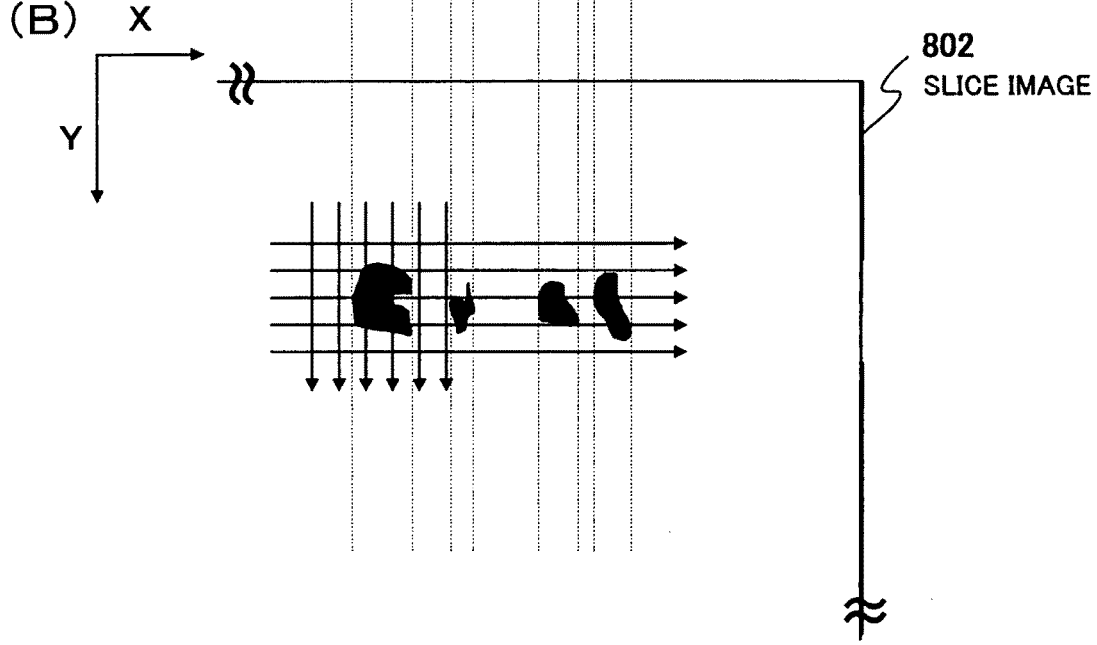

Next, with reference to FIG. 7, there will be described a case where the degree of progress of osteoporosis of the spine is quantified to some degree by making use of the average area of hollow portions of the bone. The average area may be used as a pseudo volume. In FIG. 7, hollow portions of the bone are shown in a schematic manner. Since the hollow portions differ in shape and size, these are approximated by use of "run length" and "density difference."

FIG. 7(A) is a view of a bone as viewed along the Y direction, and shows a cross section of the bone along the Z direction in an easily understandable manner. FIG. 7(B) is a view of the bone as viewed along the Z direction and shows an example slice image with a predetermined slice thickness in the Z axis direction. The slice image 802 of FIG. 7(B) is a tomogram at a slice position 801 of FIG. 7(A).

The CPU 10 obtains the average of run lengths for each direction (X, Y, Z) of the three-dimensional coordinate system. That is, the CPU 10 scans an image along the X direction to thereby obtain the average X_RL of run lengths, scans the image along the Y direction to thereby obtain the average Y_RL of run lengths, and scans the image along the Z direction to thereby obtain the average Z_RL of run lengths. The CPU 10 obtains the product of X_RL and Y_RL as the average area of the hollow portions, and the product of the average area and Z_RL as the average volume, by making use of the run lengths obtained for the respective directions.

When the slice thickness of the tomogram is large (e.g., 5 to 10 mm), the run length Z_RL in the Z direction cannot be obtained. Therefore, a "density difference $\Delta CT$" is used in place of the run length Z_RL. Here, the density difference $\Delta CT$ is obtained from the difference between the average CT value of the cancellous bone and the average CT value of low-density regions RG. That is, the average volume is approximated by the product of the average area, a constant, and $\Delta CT$.

In the above description, the degree of progress of osteoporosis is measured by use of run lengths for each direction (X, Y, Z) of the three-dimensional coordinate system. However, as described below, the degree of progress of osteoporosis may be defined by use of the run length in the X direction, the run length in the Y direction, and the density difference $\Delta CT$, or a combination thereof may be defined as the degree of progress of osteoporosis.

The degree of progress of osteoporosis is proportional to the reciprocal of {the average (avCT) of CT values (within a single image) of the cancellous bone−CTc}.

Here, CTc is an experimental value adjusted to coincide with the results of measurement by a micro CT or the like. However, it can be approximated by the CT value (e.g., about 90) of the soft bone tissue.

Thus, diagnostic assistance of higher accuracy can be performed by comparing the average CT value and the measured characteristic quantity of a spine region of the extracted original image with the actual degree of progress of osteoporosis measured in advance by use of a micro CT apparatus or the like.

When a reconstruction normalization constant is represented by S (=1/the average of cancellous bone areas (of N images), a slice thickness normalization constant is represented by T1 (thickness), and an addition constant depending on the slice thickness normalization constant (S) is represented by T2 (thickness), the degree of progress of osteoporosis can be represented by the following mathematical formulae 1 to 3.

(degree of progress of osteoporosis)=$f(X\_RL, Y\_RL, \Delta CT, avCT, S, T1(\text{thickness}), T2(\text{thickness}))$  [Formula 1]

(degree of progress of osteoporosis)=$[(X\_RL \times Y\_RL \times \Delta CT)/\{(avCT-CTc) \times S\}] \times T1(\text{thickness}) + T2(\text{thickness})$  [Formula 2]

(degree of progress of osteoporosis)=$[(X\_RL^{\alpha} \times Y\_RL^{\alpha} \times \Delta CT^{\beta})/\{(avCT-CTc)^{\gamma} \times S\}] \times T1(\text{thickness}) + T2(\text{thickness})$  [Formula 3]

The degree of progress of osteoporosis may be replaced with a run length in a direction shifted from the X-axis direction by 45 degrees (in general, an arbitrary angle), and a run length in a direction shifted from the Y-axis direction by 45 degrees (in general, an arbitrary angle). Further, the average of a plurality of substitutes may be used as the degree of progress of osteoporosis. For example, in the case of a slice of 10 mm thickness, when T1 is set to 1000.0, and T2 is set to 0.0, the degree of progress of osteoporosis (the porosity representing density) can be represented within a range of 0 to 10.

When high accuracy is not required, the degree of progress of osteoporosis can be determined while 1/(avCT−CTc) is approximated by (constant value−avCT). In this case, the degree of progress of osteoporosis can be represented by the following mathematical formula 4.

(degree of progress of osteoporosis)=$[(X\_RL \times Y\_RL \times \Delta CT)/S \times (\text{constant value} - avCT)] \times T1(\text{thickness}) + T2(\text{thickness})$  [Formula 4]

Figure 8:
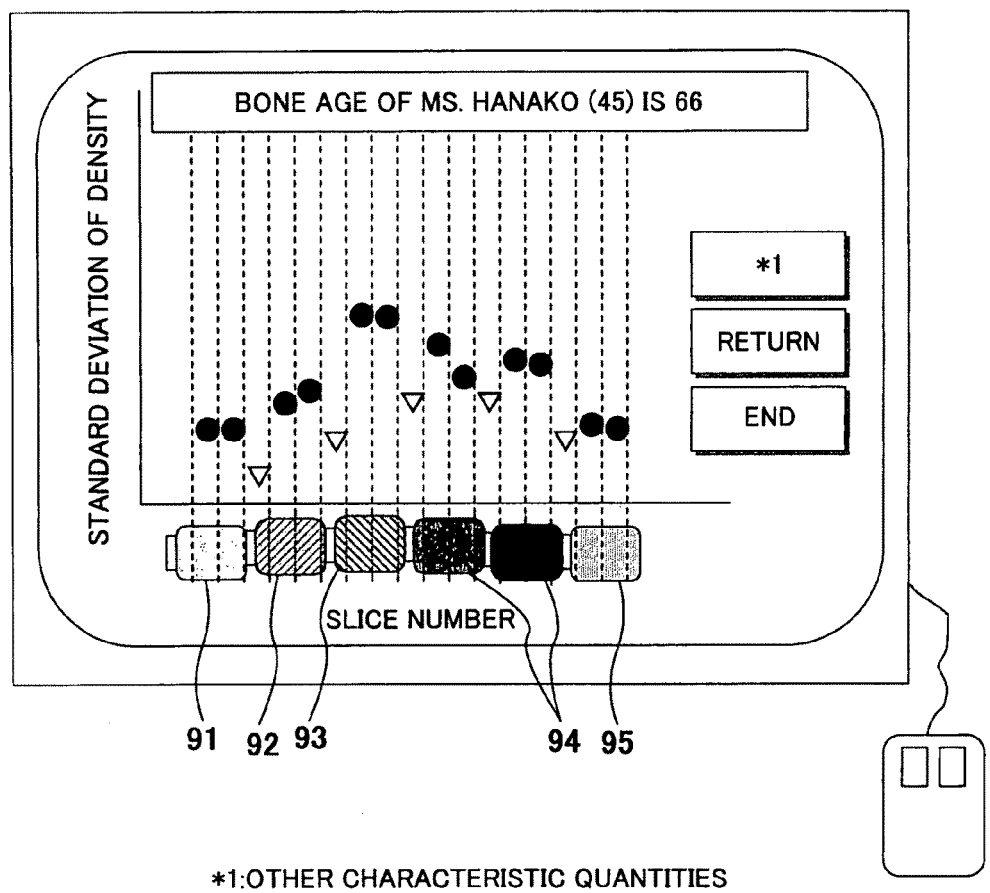
FIG. 8 Illustration showing an example relation between pseudo volume and slice position.
Figure 9:
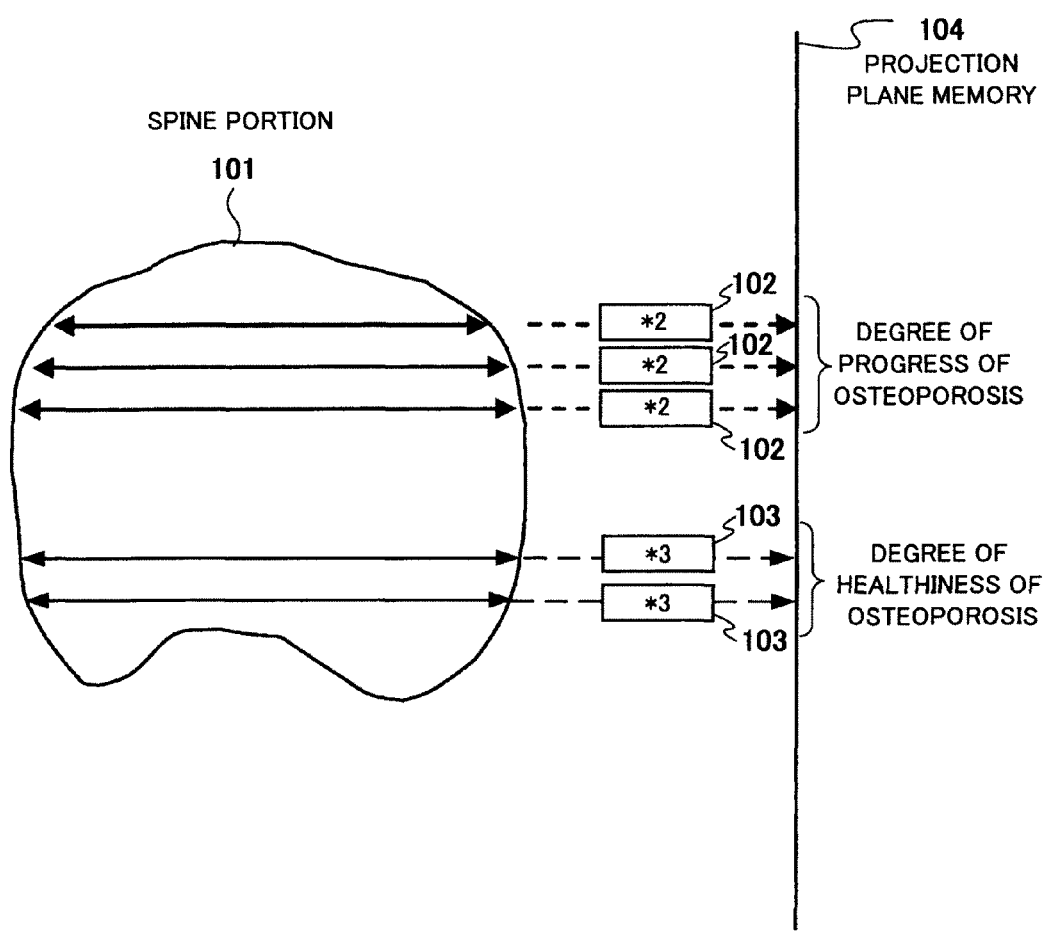
FIG. 9 Illustration showing an example case where the minimum values of CT values of a spine portion are projected onto a projection plane memory.

FIG. 8 is an illustration showing an example relation between pseudo volume and slice position. In FIG. 8, spine portions corresponding to slice positions are displayed while being colored in accordance with pseudo volume. The spine portions 91 to 95 are colored in blue, yellow, red, light red, and blue, in this sequence from the left side. With this display, the degree of progress of osteoporosis can be easily recognized. Further, when this is presented to a subject as a diagnostic result, the subject can easily understand the diagnostic result. Here, the standard deviation of CT value densities is used as a pseudo volume. The density of the spine portion may be shown by a 3D display, or projection of the maximum values or minimum values perpendicular to the body axis located within the spine or in the vicinity of the center of the spine. FIG. 9 is an illustration showing an example case where the minimum values of CT values of a spine portion are projected onto a projection plane memory. In the case where the "degree of progress of osteoporosis" is to be displayed, an image contributing to diagnosis can be obtained through use of values obtained by projecting the minimum values 102 of CT values of a spine portion 101 onto a projection plane memory 104. In the case where the "degree of healthiness (degree of normality)" is to be displayed instead of the "degree of progress of osteoporosis," there are used values obtained by projecting the maximum values 103 of CT values of the spine portion 101 onto the projection plane memory 104. Further, when the "degree of healthiness (degree of normality)" is displayed, a tomogram corresponding to the maximum value of the characteristic quantity (pseudo volume) may be displayed automatically. In this case, an anomaly message may be displayed in order to display an anomaly having occurred in the middle of processing or an anomaly of the original image.

Figure 10:
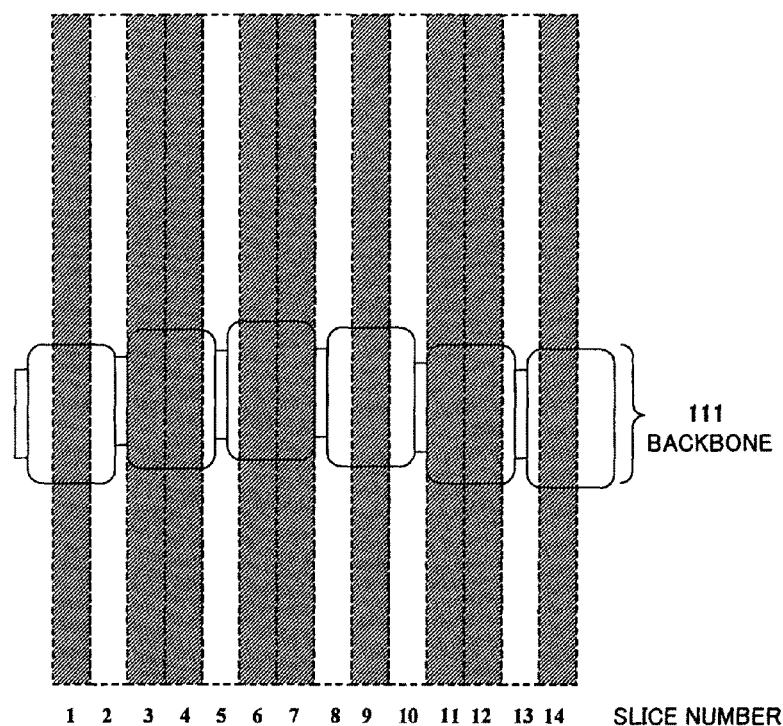
FIG. 10 Illustrations showing an example process for a case where CT values of the cancellous bone are low.
Figure 10:
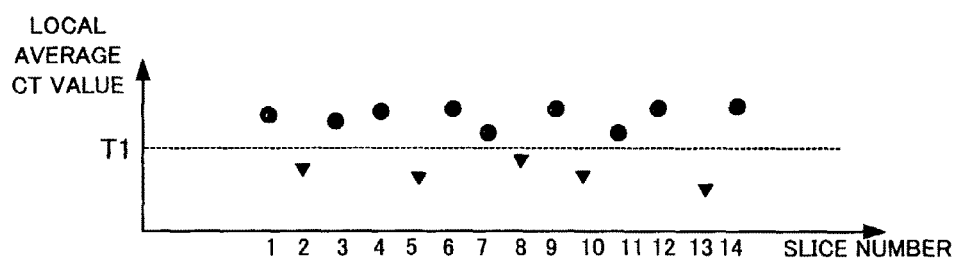

When a CT value of the cancellous bone is low, preferably, determination as to whether the corresponding portion is a joint portion of the spine is performed, and the shape of that portion is displayed, or that portion is colored on the basis of the results of the determination such that that portion can be identified. FIG. 10 is a pair of illustrations showing an example process performed for a case where CT values of the cancellous bone are low. As shown in FIG. 10, slice positions where the local average CT value is lower than a predetermined value T1 are considered to constitute joint portions of the spine, and are represented by ▼ as shown in the drawing. In FIG. 10, since the local average CT values at the slice positions of slice numbers 2, 5, 8, 10, and 13 are lower than the predetermined value T1, portions corresponding to these slice numbers are indicated by ▼. In FIG. 8, portions corresponding to these slice numbers are indicated by ▽ instead of ▼. Notably, the predetermined value T1 may be changed by dragging operation performed by use of the mouse. Alternatively, the predetermined value T1 may be automatically determined by use of a graph showing the frequencies of occurrence of slice positions at which the local average CT value is lower than the predetermined value T1. Further, when 2D-RL is greater than (the average+$\delta 1$), the shape of that portion is changed, or that portion is colored differently. Similarly, when the area of a region falls outside the range of (the average±$\delta 2$), the shape of that portion is changed, or that portion is colored differently.

Figure 11:
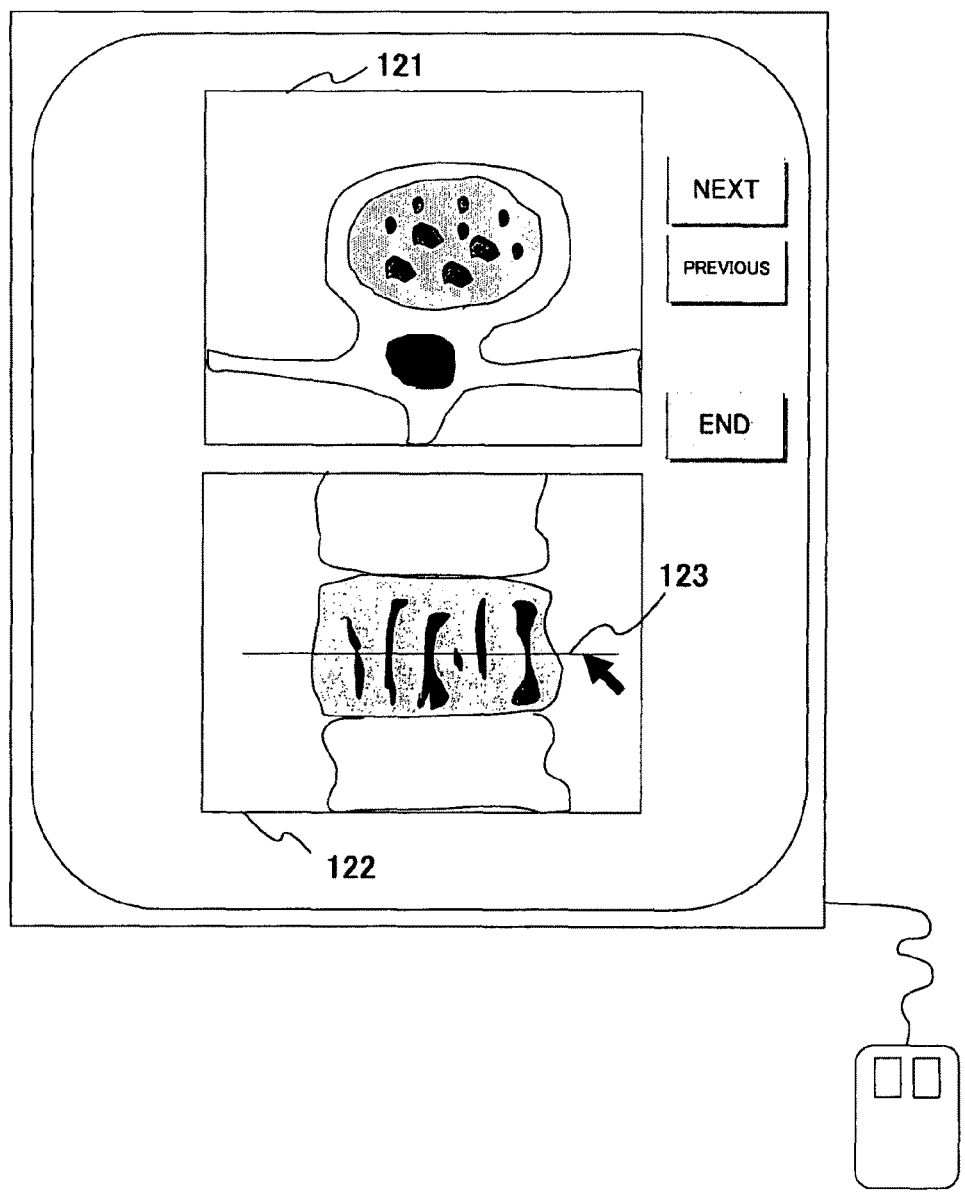
FIG. 11 Illustration showing an example screen on which an original image and colored low-density portions of a cancellous bone are superimposed.

FIG. 11 is an illustration showing an example screen on which an original image and colored low-density portions of a cancellous bone are superimposed. In FIG. 11, a cross sectional image 121 at the current slice position is displayed at an upper portion of the screen, and an image 122 in which low-density portions are colored (although the actual color is red, in the drawing, these portions are illustrated by hatching) is displayed at a lower portion of the screen. The colored portions correspond to cancellous bones in the spine. A straight line 123 provided on the image 122 can be dragged by means of the mouse or the like. As the position of the straight line 123 is changed through dragging with the mouse, cross sectional images at different positions are successively updated and displayed.

Figure 12:
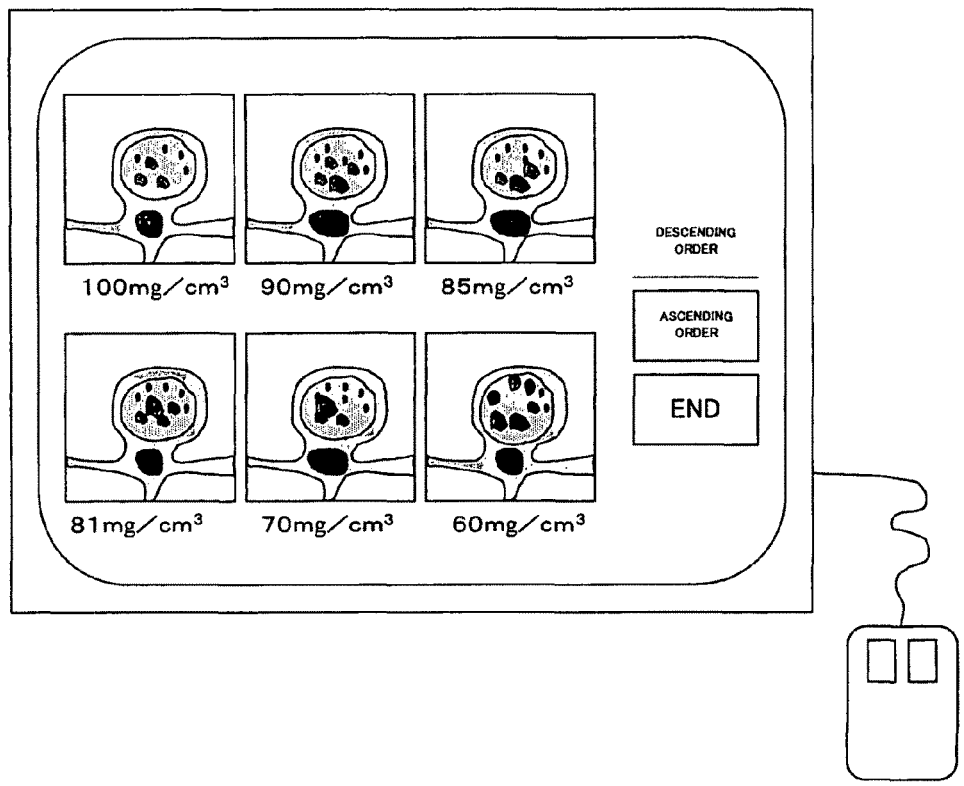
FIG. 12 Illustration showing an example screen on which images are displayed in a descending order or an ascending order of the density of hydroxyapatite contained in the cancellous bone.

FIG. 12 is an illustration showing an example screen on which images are displayed in descending order or ascending order of the density of hydroxyapatite contained in the cancellous bone. In FIG. 12, images are displayed in descending order of the density of hydroxyapatite from the upper left to the upper right, to the lower left, and then to the lower right.

Figure 13:
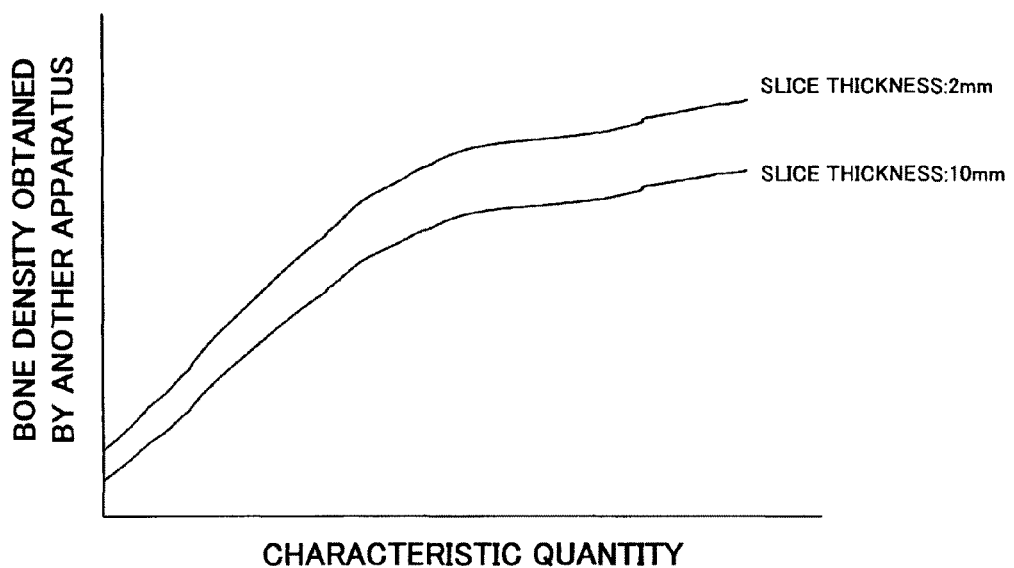
FIG. 13 Illustration showing an example case where the relation between characteristic quantity and hydroxyapatite density is obtained in advance.

FIG. 13 is an illustration showing an example case where the relation between characteristic quantity and hydroxyapatite density is obtained in advance. The vertical axis of FIG. 13 represents bone density, values of which are measured for each slice thickness by use of a micro CT apparatus or the like.

Figure 14:
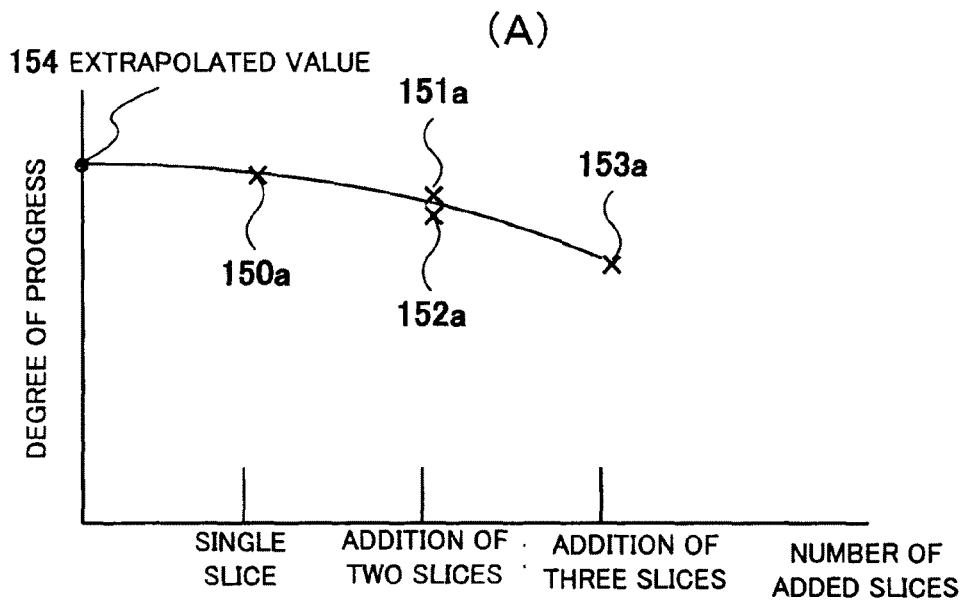
FIG. 14 Illustrations showing an example case where a characteristic quantity for zero slice thickness is obtained on the basis of characteristic quantities obtained through addition of adjacent images.
Figure 14:
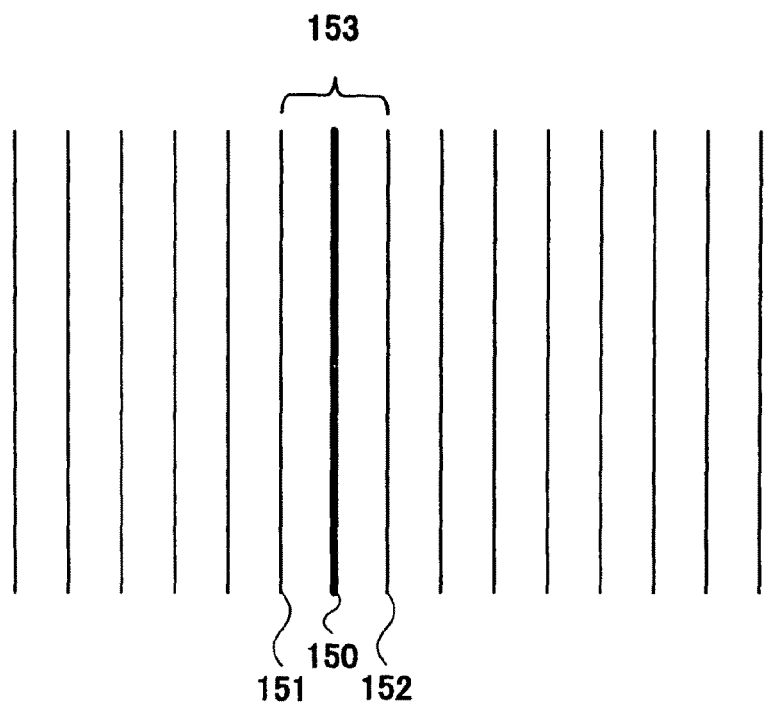

FIG. 14(A) is an illustration showing an example case where a characteristic quantity which does not depend on the slice thickness is obtained from an extrapolated value of characteristic quantities of slices, and normalized. FIG. 14(B) is an illustration showing slice images which are added so as to calculate the extrapolated value. In general, the characteristic quantity depends on the slice thickness. Therefore, as shown in FIG. 14, adjacent images are added so as to obtain a characteristic quantity for a thicker image, and an extrapolated value 154, which is the value obtained through extrapolation for an image not depending on the slice thickness, may be used as the degree of progress of osteoporosis. That is, the characteristic quantity obtained for a slice 150 is represented by 150a, the characteristic quantity obtained for the case where a leftward adjacent slice 151 is added to the slice 150 is represented by 151a, the characteristic quantity obtained for the case where a rightward adjacent slice 152 is added to the slice 150 is represented by 152a, and the characteristic quantity obtained for the case where both the slices 151 and 152 are added to the slice 150 is represented by 153a. An extrapolated value obtained from a curve created by plotting these characteristic quantities 150a, 151a, 152a, and 153a is used as a characteristic quantity which does not depend on the slice thickness so as to determine the degree of progress of osteoporosis or the like.

Accordingly, the relation between characteristic quantity and body calcium is previously obtained, and by making use of the relation between age and body calcium, a message "The bone age of Ms. Hanako (45 years old) is 66." as shown in FIG. 8 is displayed on the screen. Further, the actual age and the bone age corresponding to the degree of progress of osteoporosis are displayed.

Thus, the degree of progress of osteoporosis can be recognized in a manner correlated with aging.

Figure 15:
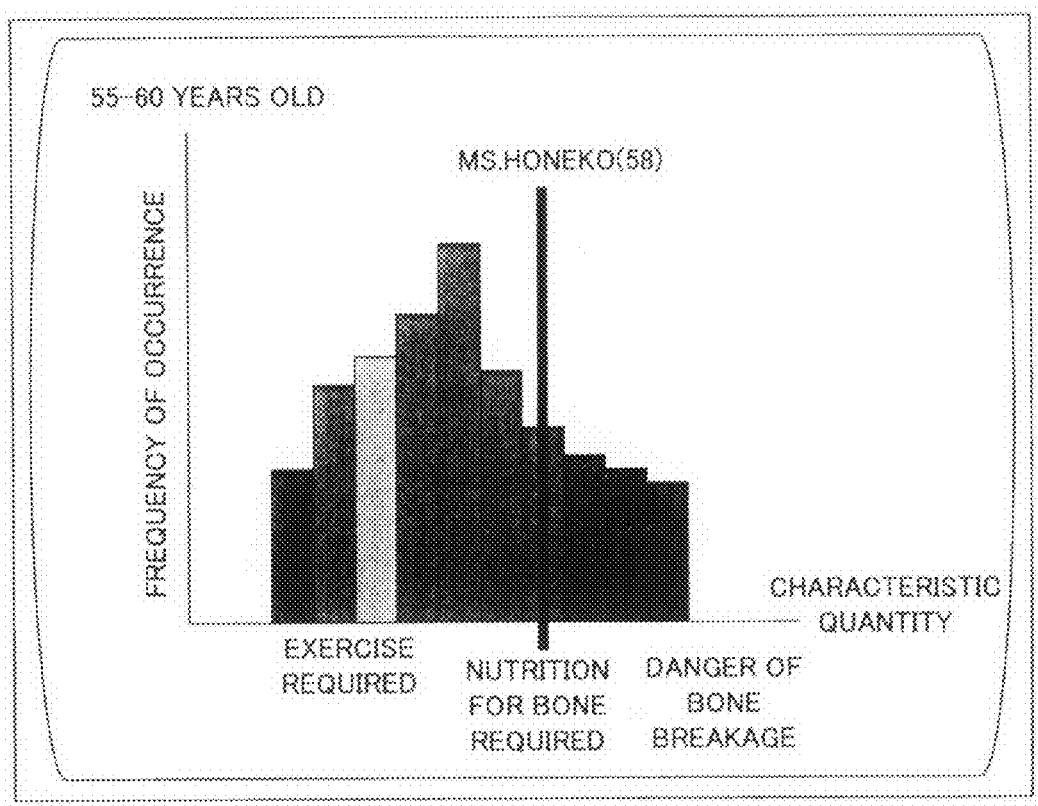
FIG. 15 Illustration showing an example relation between occurrence frequency and characteristic quantities of peoples of 55 to 60 years old.

FIG. 15 is an illustration showing an example relation between occurrence frequency and characteristic quantities of persons who are 55 to 60 years old. If the relation between occurrence frequency and characteristic quantity at a certain age is obtained in advance, warnings such as "nutrition for bone is necessary" can be provided for "Ms. Honeko," who is a person having a medical examination.

In the above description, attention is paid to destroyed portions. However, attention may be paid to a bone portion remaining undestroyed. In this case, run lengths of a white (high density) portion in FIG. 7 are used. The degree of healthiness can be represented by the following mathematical formula 5.

$$(\text{degree of healthiness}) = X\_RL \times Y\_RL \times (avCT - CTc) / (\Delta CT \times S) \qquad \text{[Formula 5]}$$

In this formula, avCT represents the average CT value of the cancellous bone portion, $\Delta$CT represents a value obtained by subtracting the avCT from the average of CT values of a high density portion, and S represents the area of the cancellous bone portion.

Figure 16:
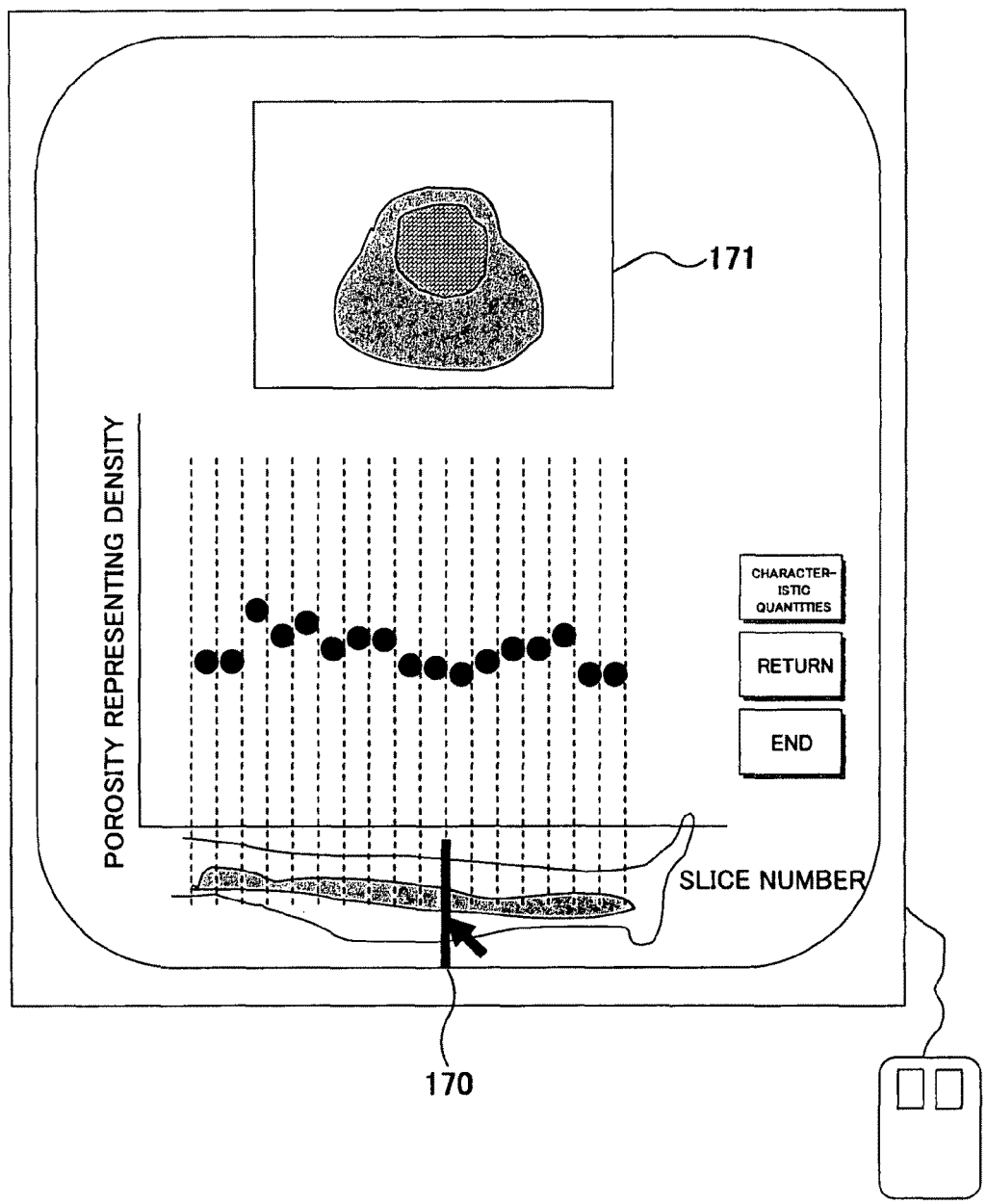
FIG. 16 Illustration showing an example relation between pseudo volume and slice position for a leg bone.

FIG. 16 is an illustration showing an example relation between pseudo volume and slice position for a leg bone. Here, as in the case of the spine, the standard deviation of CT value density is used as a pseudo volume. A cross sectional image 171 at the position of a straight line 170 moved by use of the mouse is displayed at an upper portion of the screen. Accordingly, when the straight line 170 is dragged by use of the mouse or the like, the cross sectional image 171 is successively updated and displayed with a different cross sectional image corresponding to the moved position of the straight line 170.

Figure 17:
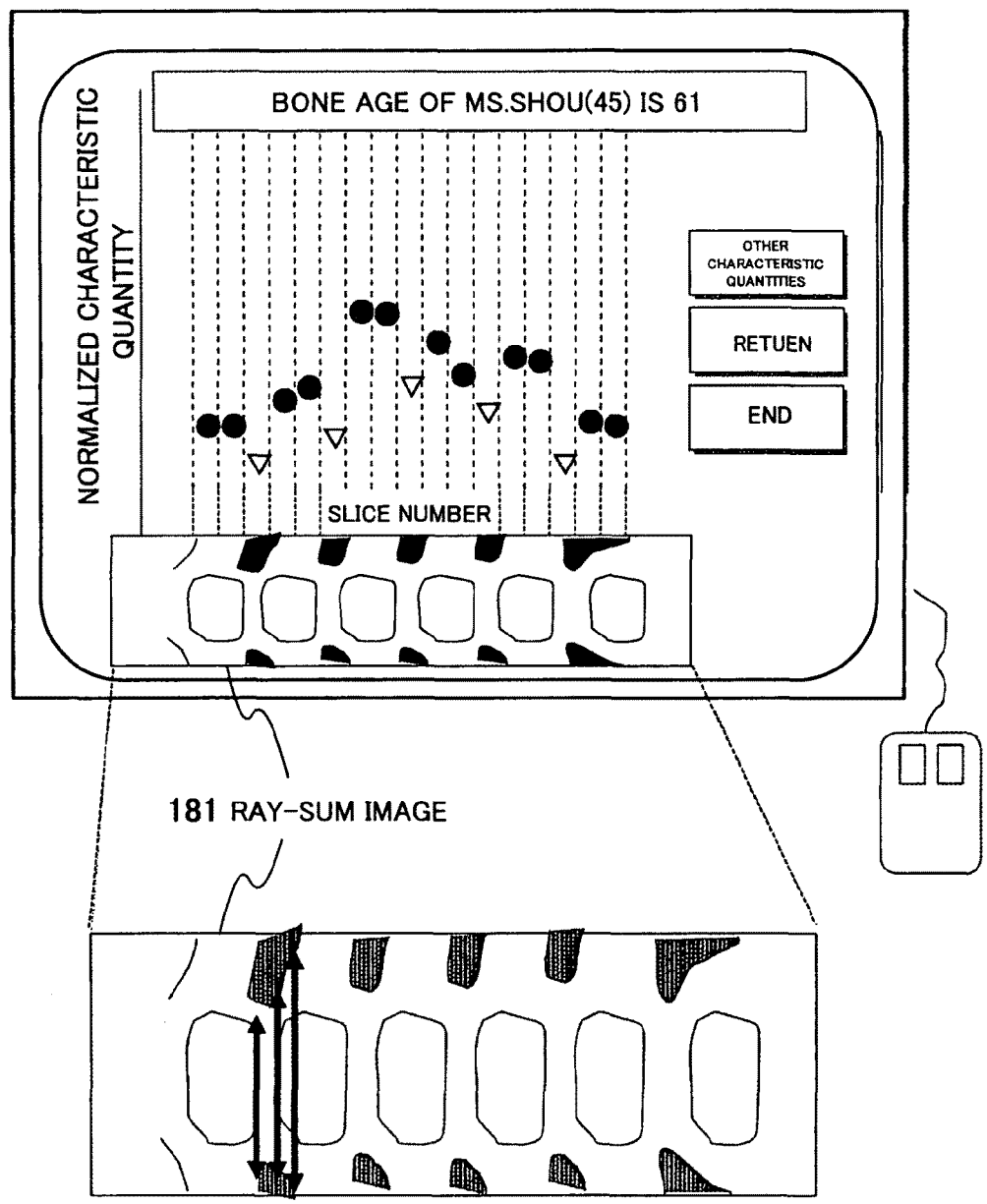
FIG. 17 Illustration showing an example relation between normalized characteristic quantity and slice position.

FIG. 17 is an illustration showing an example relation between normalized characteristic quantity and slice position. That is, FIG. 17 shows the density (CT value) of a spine region of a subject as viewed from the front by use of a normalized characteristic quantity. A mark "●" is displayed at a position corresponding to the magnitude of the normalized characteristic quantity of a spine portion corresponding to each slice position. In FIG. 17, each joint portion of the spine is indicated by "V." Here, the joint portion of the spine is determined on the basis of a ray-sum image. That is, the length of each low-CT-value portion of the ray-sum image is examined, and when the length is shorter than those of spine portions on opposite sides in the left-right direction, that portion is determined to be a joint of the spine.

Figure 18:
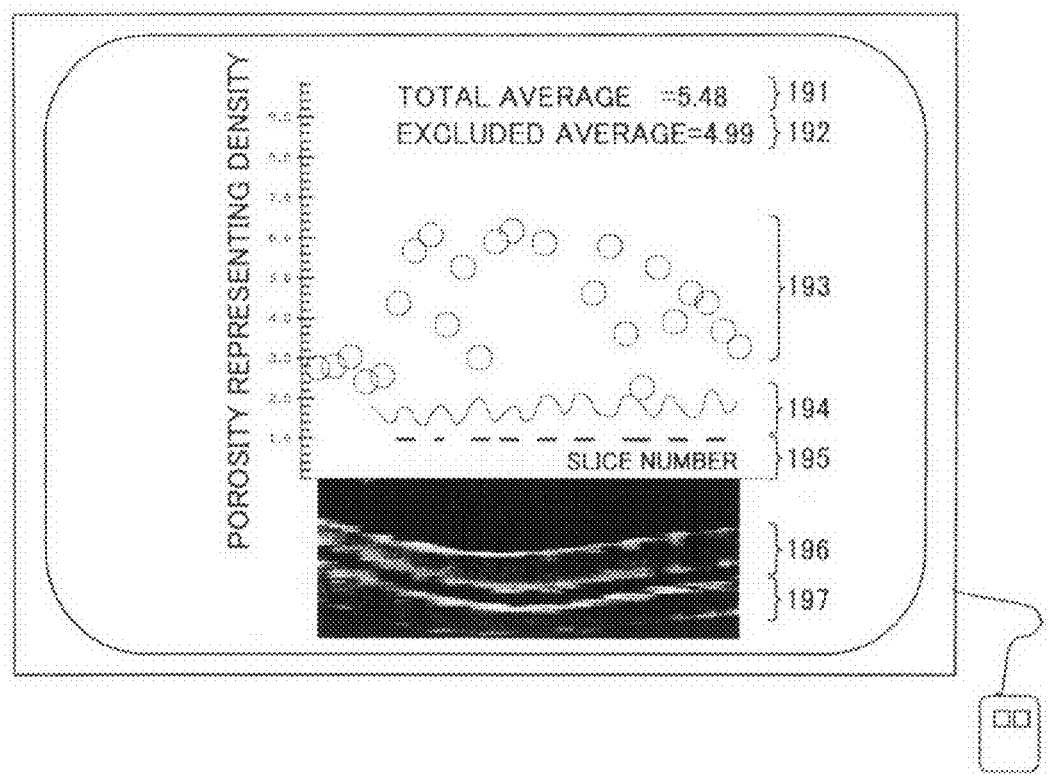
FIG. 18 Illustration showing a relation a characteristic quantity of a patient suffering osteoporosis and an image used for calculation of the characteristic quantity.
Figure 19:
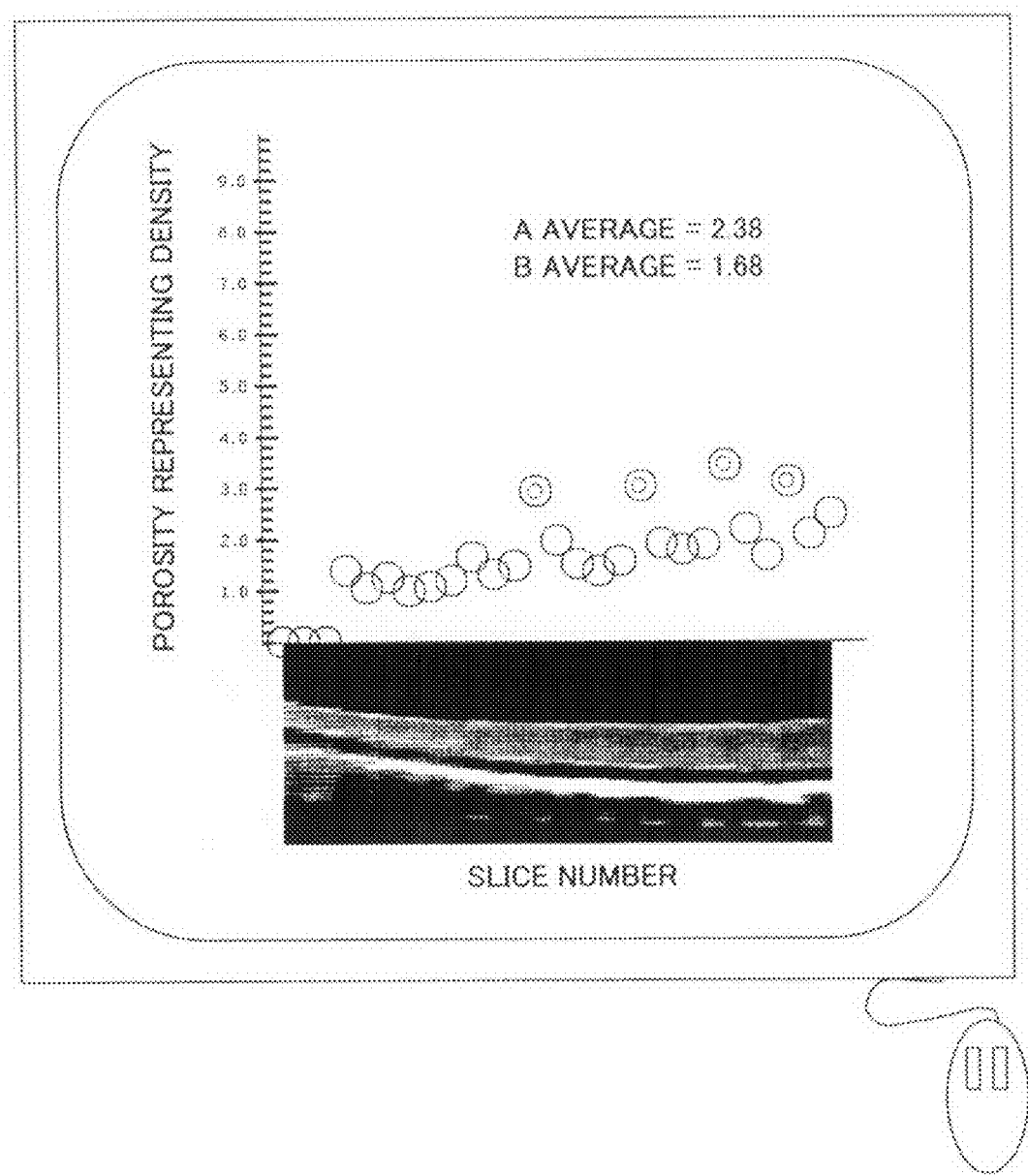
FIG. 19 Illustration showing a relation between a characteristic quantity of a healthy person and an image used for calculation of the characteristic quantity.

FIG. 18 is an illustration showing an example relation between a characteristic quantity of a patient suffering osteoporosis and an image used for calculation of the characteristic quantity. FIG. 19 is an illustration showing an example relation between a characteristic quantity of a healthy person and an image used for calculation of the characteristic quantity.

A display section 191 shows the average of all points; a display section 192 shows the average for the case where concave portions of a curve in a display section 194 are removed; a display section 193 shows measurement (calculation) points; the display section 194 shows the CT average of the cancellous bone region; a display section 195 shows convex portions of the curve in the display section 194; a display section 196 shows the average CT value of the cancellous bone region; and a display section 197 shows the average CT value of a lower portion of the spine bone.

In order to show the position, an image of a region of interest is disposed along the horizontal axis of the graph FIG. 18. The position of this image of the region of interest is not limited to the below graph, but may be disposed above the graph or along the vertical axis (in this case, the horizontal axis shows the characteristic quantity). In FIG. 18, the degree of progress of osteoporosis, which is the characteristic quantity, is displayed as "porosity representing density." As shown in FIG. 18, the "porosity representing density," which is the characteristic quantity, has different values at different positions along the spine. However, in the case of a patient suffering osteoporosis, the porosity representing density changes greatly as compared with the case of a healthy person. The spine (backbone) which supports the human body and serves as an axis, is composed of 7 cervical vertebrae, 12 thoracic vertebrae, 5 lumbar vertebrae, a sacrum, and a coccyx, as viewed from the head. A cushion formed of cartilaginous bone called an intervertebral disk is present between adjacent spine bones. The spine bone and the intervertebral disk greatly differ in CT value. That is, when calculation is performed by use of a CT image containing a large intervertebral disk region, the calculation result shows a large value. Accordingly, simple averaging results in a failure to obtain the characteristic quantity regarding the spine bone. As can be understood from the characteristic quantity of a normal person (healthy person) of FIG. 19, the values at portions indicated by double circles (joint portions) have large degrees of irregularity. In view of this, preferably, the joint portions of the spine are extracted as described above, and the average of the characteristic quantities of the remaining portions is obtained. Further, a different method for extracting the joint portions of the spine will be described. Regions of interest for which characteristic quantities are obtained, and the obtained characteristic quantities are classified on the basis of anatomical data.

Figure 20:
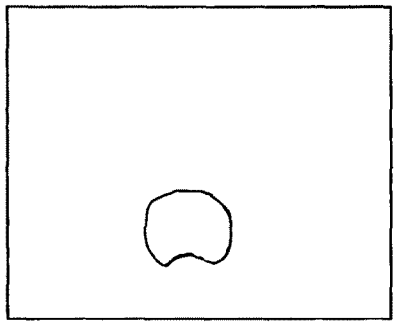
FIG. 20 Illustrations showing cancellous bone regions in different slices.
Figure 20:
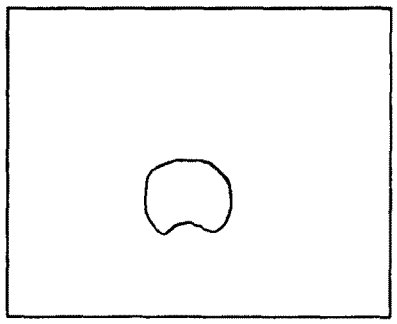
Figure 20:
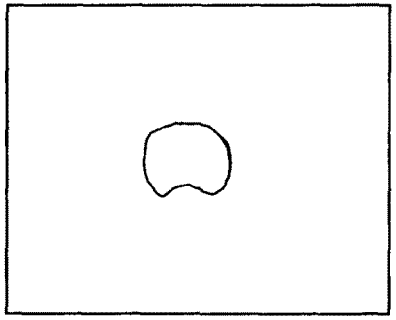
Figure 20:
Figure 20:
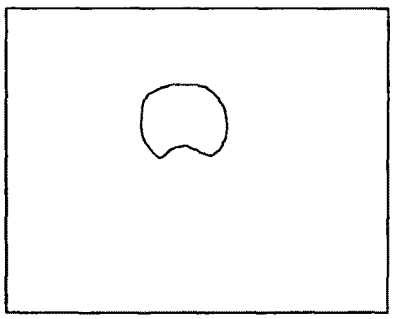
Figure 21:
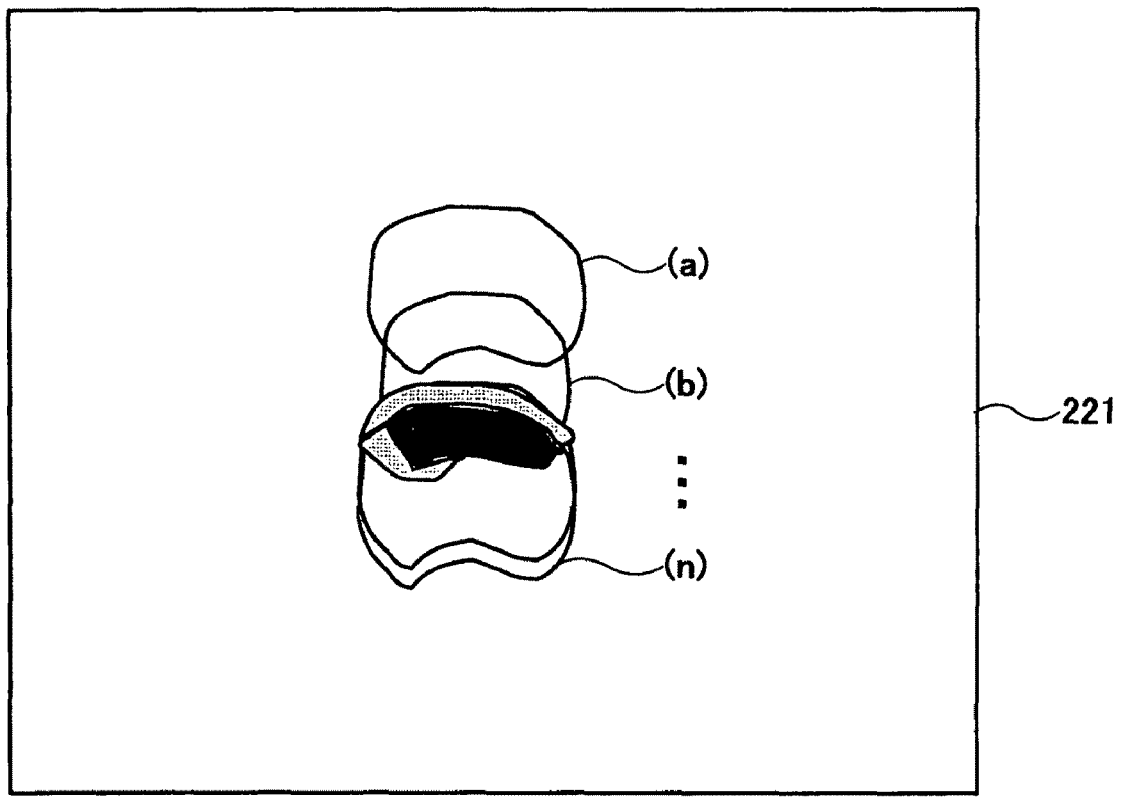
FIG. 21 Illustration showing extraction of an overlap region where the cancellous bone regions in the different slices overlap one another.

First, there will be described a different method for extracting the joint portions of the spine in which overlapping of cancellous bones in different slices is utilized. FIG. 20 is a set of illustrations showing cancellous bone regions in different slices. The number of slices is n, and the position of the cancellous bone changes gradually as shown in FIGS. 20(a) to 20(n). This is because a portion of the backbone in the vicinity of the head slightly curves upward and/or the entire backbone curves in some patients. FIG. 21 is an illustration showing extraction of an overlap region from the cancellous bone regions in the different slices of FIG. 20. That is, a common region (logical product region) of the cancellous bone regions of FIGS. 20(a) to 20(n) is calculated. In an image 221 shown in FIG. 21, a thick hatched portion shows the maximum region where the overlapping becomes the maximum. Thus, the characteristic quantity is extracted through use of images of slices including cancellous bone regions containing the maximum region. Notably, the images of slices which are greater than a predetermined value in terms of the degree of overlapping with the maximum region may be used for calculation of the characteristic quantity.

Figure 22:
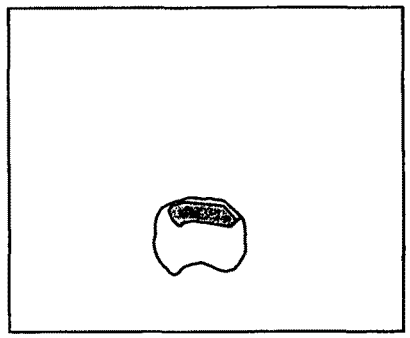
FIG. 22 Illustrations showing the overlapping between the maximum region and the cancellous bone regions in the slices of FIG. 20.
Figure 22:
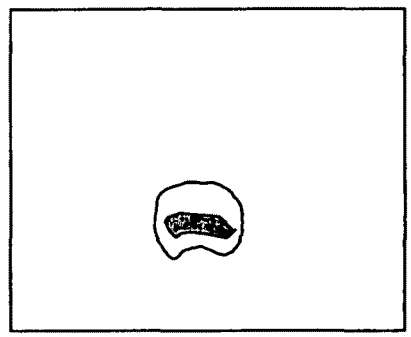
Figure 22:
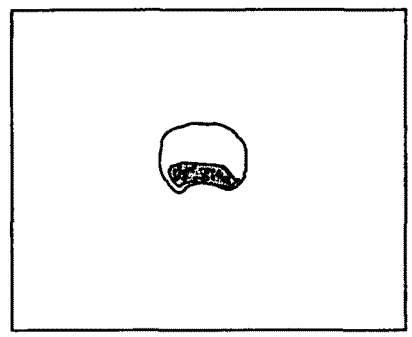
Figure 22:
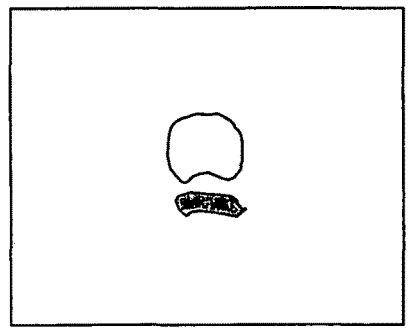

FIG. 22 is a set of illustrations showing the overlapping between the maximum region and the cancellous bone regions in the different slices of FIGS. 20(a) to 20(n). Although slices whose cancellous bones completely overlap the maximum region as shown in FIGS. 20(a) to 20(c) are used for calculation of the characteristic quantity, slices whose cancellous bones do not overlap the maximum region as shown in FIG. 20(n) are not used for calculation of the characteristic quantity. Slices whose degree of overlapping is greater than a predetermined value are used for calculation of the characteristic quantity. Alternatively, selection of slices may be performed as follows. Of tomogram images at different positions; i.e., the cancellous bone regions (regions of interest) of the slices of FIGS. 20(a) to 20(n), a region of interest whose degree of overlapping with other regions of interest is the maximum is specified, and the degree of overlapping between that region of interest and the region of interest of each tomogram image is obtained, and determination as to whether each tomogram image is to be used for extraction of the characteristic quantity is performed on the basis of the degree of overlapping.

In many cases, regions whose densities are lower than the average density correspond to hollow portions of the bone. Therefore, hollow portions of the original image can be displayed in a recognizable manner by superimposing these regions on the original image.

Figure 23:
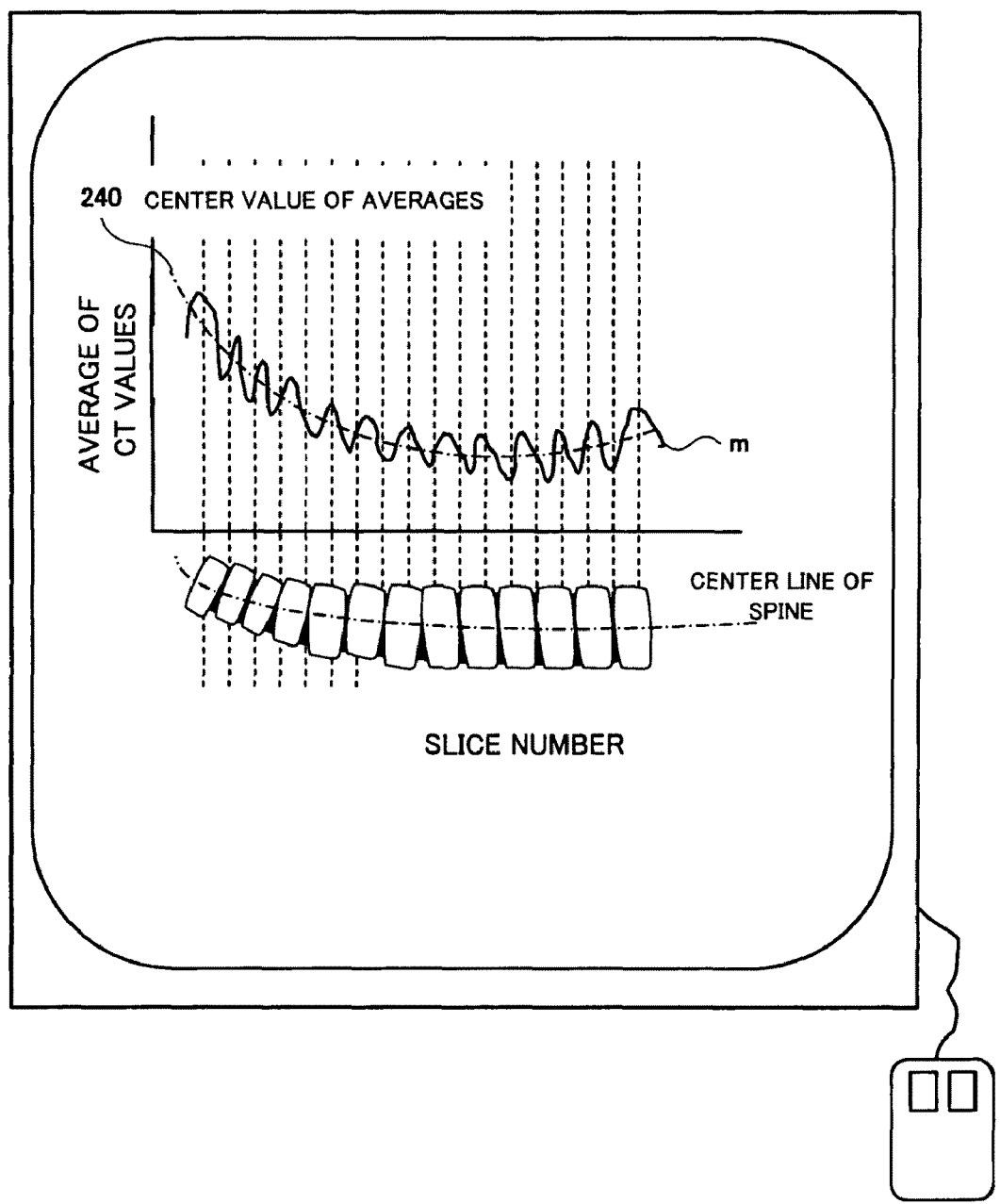
FIG. 23 Illustration showing a screen on which the average of densities (CT values) of the spine regions is plotted for the case where a human body is viewed from a lateral side.
Figure 24:
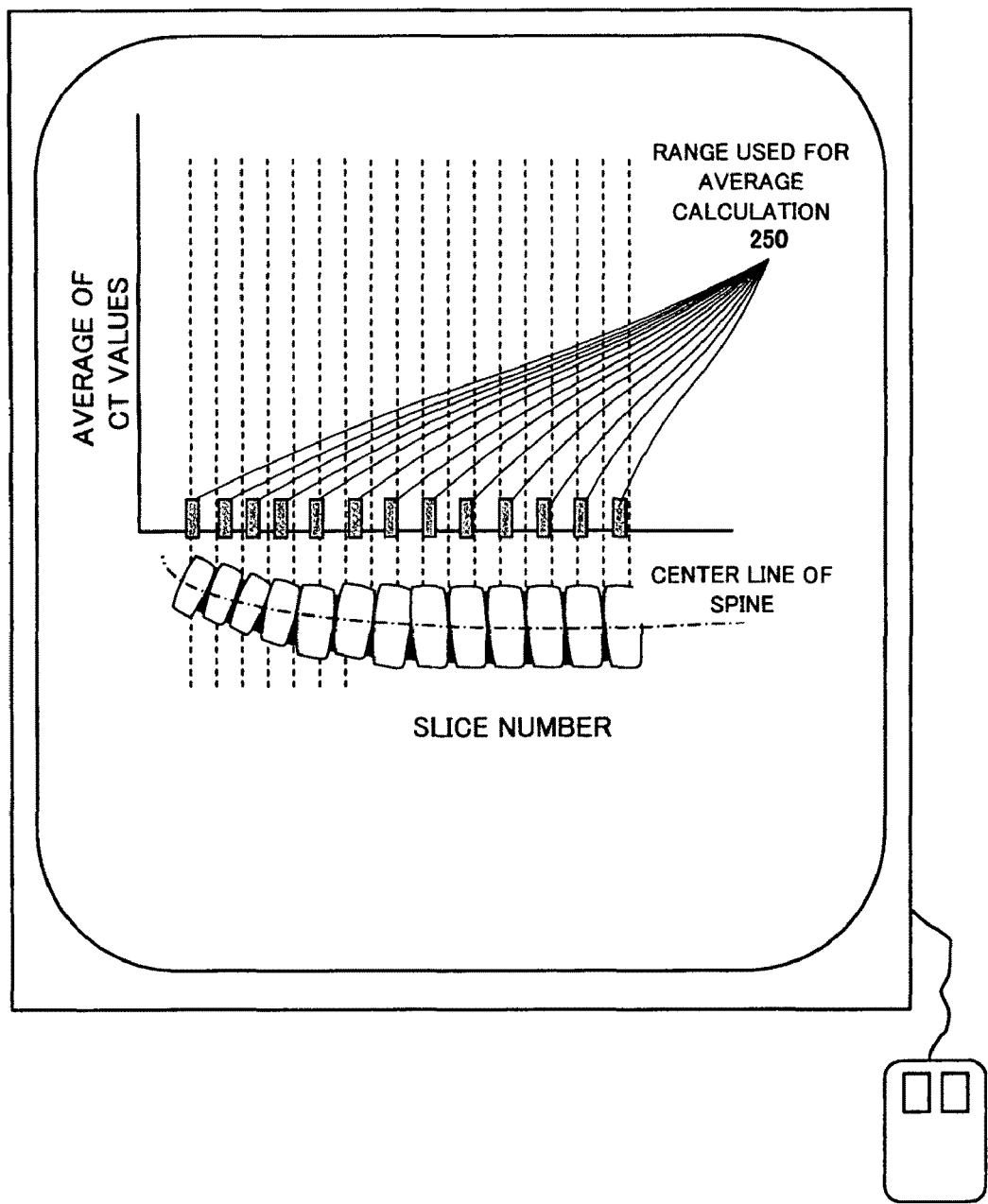
FIG. 24 Illustration showing the result obtained by extracting portions where the density (CT value) is higher than a predetermined curve.

Next, there will be described another method for extracting the joint portions of the spine in which the average of densities of the spine region is employed. FIG. 23 is an illustration showing a screen on which the average of densities (CT values) of the spine region is plotted for the case where a human body is viewed from a lateral side. As shown in FIG. 23, the density average; i.e., increases at slices containing the spine bones and decreases at slices containing the intervertebral disks. Low density portions are intervertebral disk regions, and high density portions are spine bone regions. When the degree of progress of osteoporosis (characteristic quantity) of the spine bone is to be examined, the average of high density portions is used. As shown in FIG. 23, the wave form of the density average includes repeated high portions and low portions. Therefore, the average between a high portion (portion exhibiting the local maximum) and an adjacent low portion (portion exhibiting the local minimum) is obtained, and a curve 240, which shows the center value of averages, is drawn. Portions (convex regions) where the density (CT value) is higher than the curve 240 are extracted. FIG. 24 is an illustration showing the result obtained by extracting portions (convex regions) where the density (CT value) is higher than the curve 240. As shown in FIG. 24, hatched portions 250 are the portions where the density (CT value) is higher than that indicated by the curve 240. Accordingly, the values of these hatched portions 250 are used for calculation of the degree of progress of osteoporosis of the spine bone. For convenience, the average of the hatched portions is calculated as "excluded average," the average of all the data is calculated as "total average," and the excluded average and the total average are displayed simultaneously. Further, conveniently, a warning message such as "close examination is necessary" is displayed when the excluded average or the total average exceeds a predetermined value. Meanwhile, the degree of progress of osteoporosis of the intervertebral disks can be obtained by use of the values other than those of the hatched portions 250; i.e., the values of low density portions (portions exhibiting the local minimum). Conveniently, the degree of progress of osteoporosis is displayed in, for example, 10 levels, and a warning message such as "close examination is necessary" is displayed when the average or the characteristic quantities exceeds a predetermined value. No restriction is imposed on the method of providing such a warning. Preferably, such a warning is provided by displaying a warning message, generating a warning sound, generating a warning voice, etc., which may be used singly or in combination.

Figure 25:
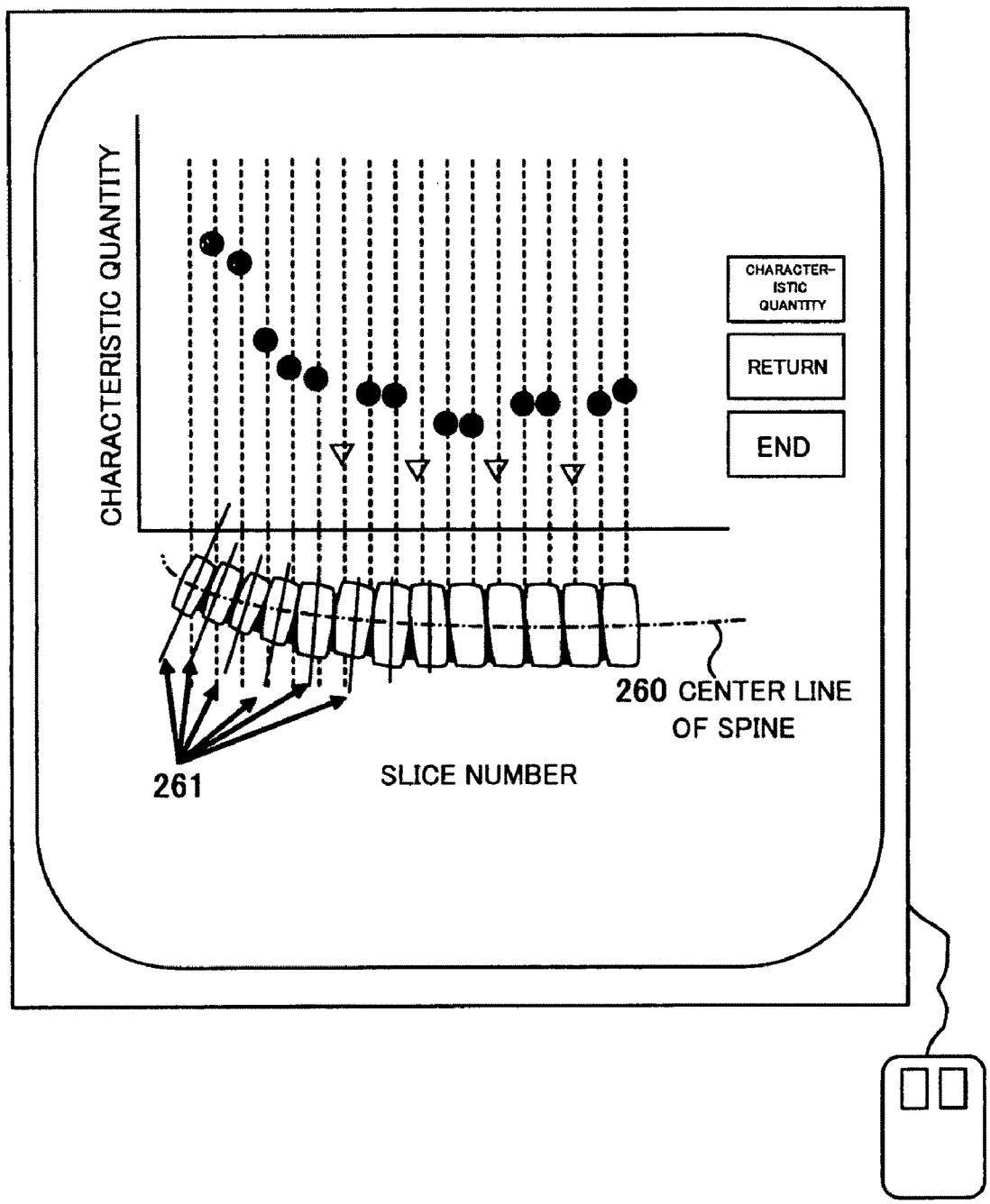
FIG. 25 Illustration showing an example case where a characteristic quantity is obtained for a spine region of a human body as viewed from a lateral side thereof.

FIG. 25 is an illustration showing an example case where the characteristic quantity is obtained for a spine region of a human body as viewed from a lateral side thereof. As shown in FIG. 25, the backbone of the human body curves in the vicinity of the head. Therefore, when characteristic quantities are extracted from such a portion on the basis of slice positions, a large error is produced. Therefore, the following procedure may be employed. The center line 260 of the spine is extracted; complementary lines 261 are drawn perpendicularly to the center line 260; and characteristic quantities of the spine portion are extracted along the complementary lines 261. With this procedure, the characteristic quantities of the curved portion of the spine can be measured accurately. Further, when the angle between a complementary line 261 and the corresponding slice plane is greater than a predetermined value, the characteristic quantity of that portion may be excluded.

Figure 26:
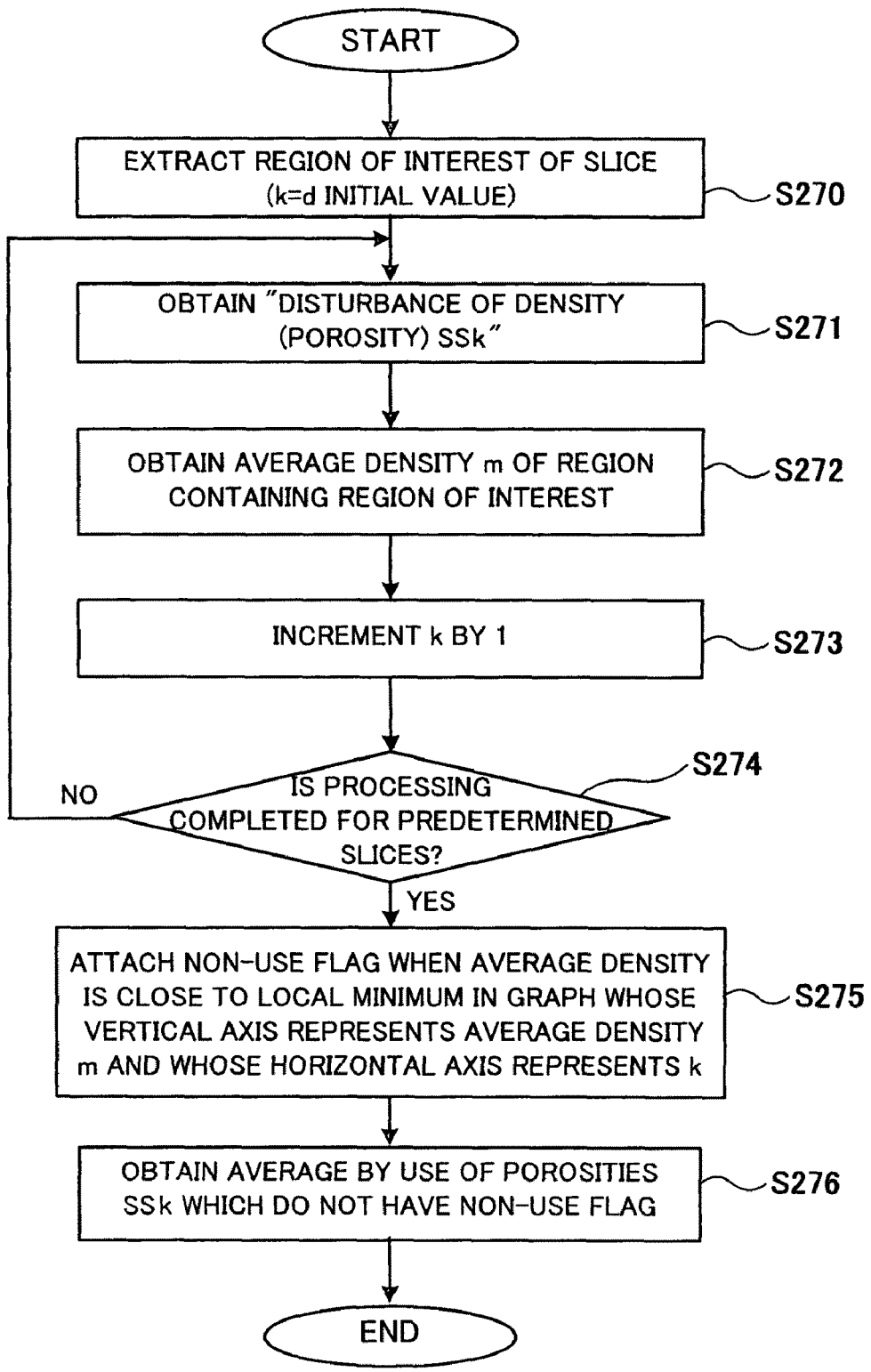
FIG. 26 Flowchart showing an example process of extracting a characteristic quantity of the spine; i.e., "porosity representing density" in consideration of joint portions of the spine.

FIG. 26 is a flowchart showing an example process of extracting a characteristic quantity of the spine; i.e., "the porosity representing density" in consideration of the joint portions of the spine. First, as in steps S50 and S51 of FIG. 4, in the first step S270, a region of interest of the first slice (k=initial value) is extracted. Specifically, the cancellous bone region of the bone is extracted by means of threshold processing or the like. By the processing of this step, the cancellous bone region in the image of each slice is extracted.

In step S271, the CPU 10 obtains the average AV of CT values of the extracted cancellous bone, and obtains the degree of progress of osteoporosis; i.e., the porosity representing density SSk, by use of the above-described calculation formulae.

In step S272, the CPU 10 obtains the average density (average of CT values) m of a region containing the region of interest as shown in FIG. 23. Subsequently, the CPU 10 displays, in a related manner, the average density of the region containing the region of interest (a specific tomogram), the obtained degree of progress of osteoporosis, and the image of the subject.

In step S273, the CPU 10 increments k by 1 so as to designate the next slice.

In step S274, the CPU 10 determines whether or not the process is completed for predetermined slices. If the CPU 10 makes a "yes" determination (the process is completed), the CPU 10 proceeds to the next step S275. If the CPU 10 makes a "no" determination, the CPU 10 returns to step S271, and executes the above-described processing.

In step S275, when the average density is close to the local minimum in the graph whose vertical axis represents the average density m and whose horizontal axis represents the slice position k as shown in FIG. 23, the CPU 10 attaches a non-use flag (∇) to the corresponding slice position.

In step S276, the CPU 10 selects the porosities SSk at the slice positions to which the non-use flag (∇) was not attached in the previous step, and obtains their average as the degree of progress of osteoporosis. In FIG. 19, the non-use flag is represented by ⊚; "A average=2.28" shows the density average obtained from the porosities at all the slice positions, including those to which the non-use flag (⊚) was attached; and "B average=1.68" shows the density average obtained from the porosities at the slice positions, excluding those to which the non-use flag (⊚) was attached. As is apparent from the above, the average which is obtained from the porosities at the slice positions, excluding those to which the non-use flag ⊚ is attached, is closer to the degree of progress of osteoporosis.

Figure 27:
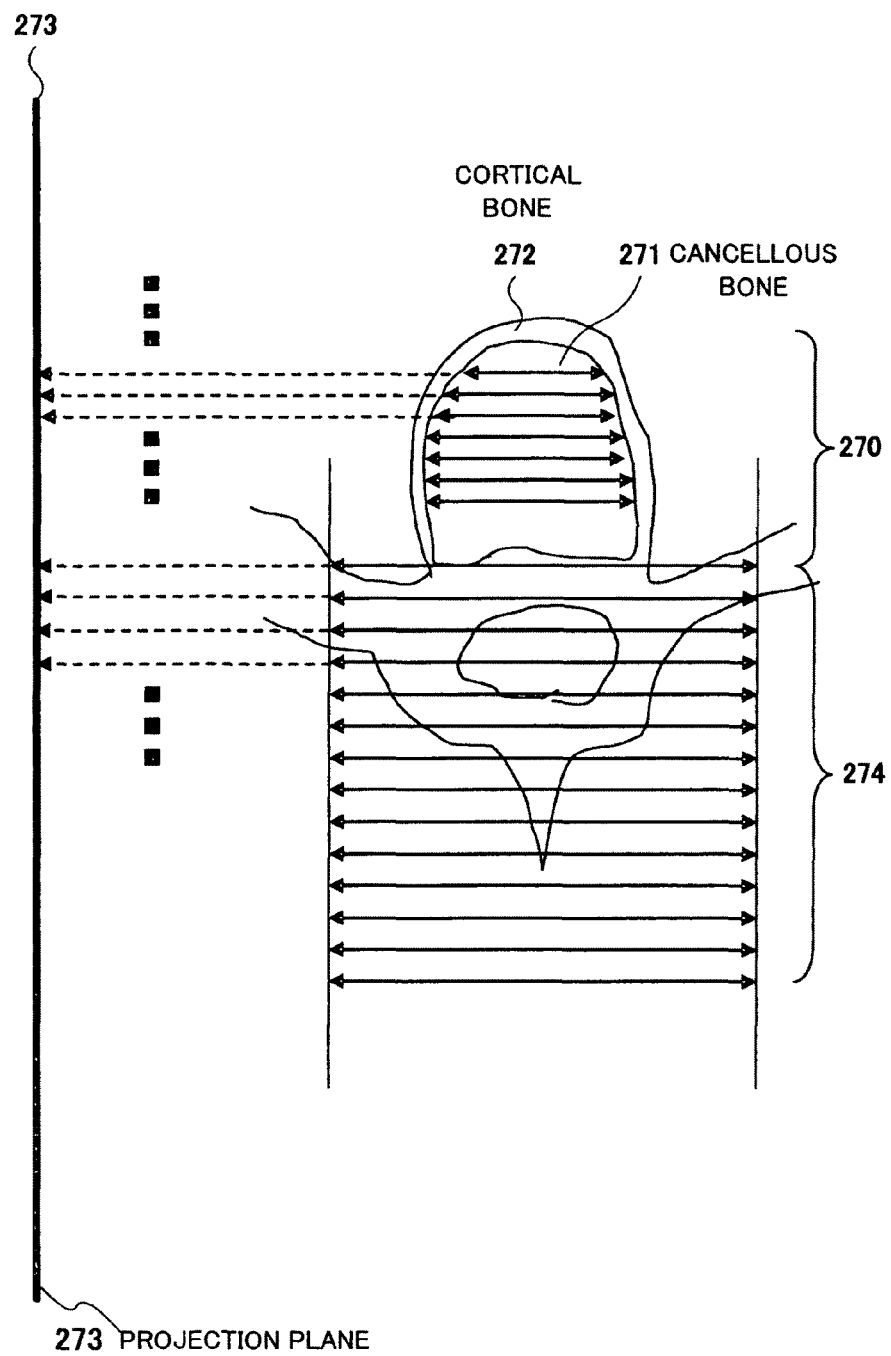
FIG. 27 Illustration for explaining picture images which are included in FIGS. 18 and 19 so as to stretch along the horizontal axis.

FIG. 27 is an illustration used for explaining images which are shown in FIGS. 18 and 19 to extend along the horizontal axis. In a region 270 containing a cancellous bone 271, the average of CT values of the cancellous bone 271 or the cancellous bone 271 and a cortical bone 272 is obtained, and projected on a projection plane 273. Further, in a region 274 which does not contain the cancellous bone 271, the density average of the region including the vicinity thereof is obtained, and projected on the projection plane 273. Images obtained through the projection are shown in FIGS. 18 and 19 such that they extend along the horizontal axis. Images used in the above description are axial images. However, sagittal images or coronal images may be used. Further, any term such as "porosity representing density," "density missing degree," or "density deficiency degree" may be used in order to represent the "degree of progress of osteoporosis."

Figure 28:
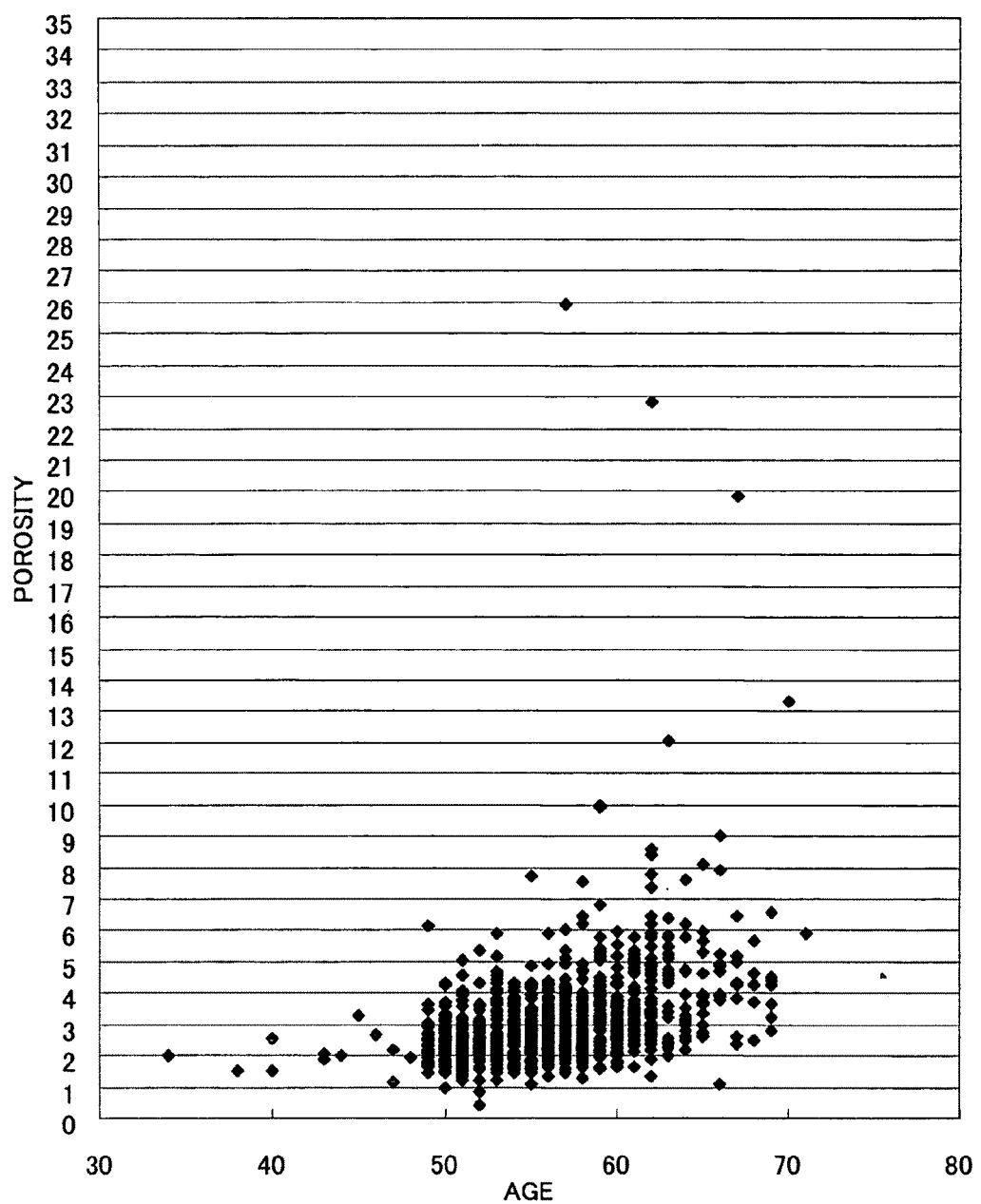
FIG. 28 Graph showing the relation between age and porosity.

FIG. 28 is a graph showing the relation between age and porosity, wherein the horizontal axis represents age, and the vertical axis represents porosity.

Since a patient does not have pain or any other subjective symptoms even when osteoporosis proceeds, in some cases the patient thinks that "I am healthy." Since the graph shown in FIG. 28 contains data of persons whose osteoporosis has progressed and data of persons whose osteoporosis has not progressed, a distribution range is wide.

In view of the above, preferably, the following procedure is employed. In the graph shown in FIG. 28, porosities corresponding to the age of a patient are selected, and when the porosity of the patient is greater than a value obtained by multiplying the average of the porosities by a constant (e.g., 1.1), this fact is notified to the patient. In this case, the patient is advised to receive guidance from a doctor, and to improve his or her diet.

This is a warning which reports that the degree of progress of osteoporosis is at a warning level and close examination is necessary. The warning information is provided to the patient by means of warning sound, warning voice, display of a warning message, or the like.

Thus, the warning information supports an examining person to correctly perform diagnosis.

Preferred embodiments of the diagnostic imaging support system according to the present invention have been described with reference to the accompanying drawings. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

The invention claimed is:

1. A diagnostic imaging support system comprising:
storage means for storing an image of a subject; and
control means for reading out the image from storage means, extracting a diagnostic region including a bone region from the read image on a basis of a characteristic quantity previously set, extracting a bone portion component and a component other than the bone portion from the diagnostic region, and calculating structure analysis information of the bone by utilizing at least one of a run length or density of a region that corresponds to the component other than the bone portion.

2. A diagnostic imaging support system according to claim 1, wherein the structure analysis information is the shape symmetry of a region representing one of a density representing the bone portion, or a portion other than the bone portion, of each of first and second regions, the first and second regions being at least two regions divided from the extracted diagnostic region.

3. A diagnostic imaging support system according to claim 1, wherein the display means displays the bone region of the subject such that the bone component and the component other than the bone can be identified by the characteristic quantity.

4. A diagnostic imaging support system according to claim 1, wherein the display means performs display, while changing a method of projecting the bone portion of the subject depending on whether the degree of progress of osteoporosis or the degree of healthiness of osteoporosis is displayed.

5. A diagnostic imaging support system according to claim 1, wherein
the extraction means determines a joint portion of the bone portion on the basis of density; and
the display means displays the joint portion of the bone in an identifiable manner on the basis of results of the determination.

6. A diagnostic imaging support system according to claim 1, further comprising
means for generating a ray-sum image of a spine region of the subject as viewed from the front, the image showing normalized densities of the spine region, wherein
the display means simultaneously displays the generated ray-sum image and the characteristic quantity of each tomogram of the subject.

7. A diagnostic imaging support system according to claim 1, further comprising
means for calculating, as a total average, an average of characteristic quantities corresponding to a plurality of bone regions of the subject and for calculating, as an excluded average, an average of the characteristic quantities excluding characteristic quantities corresponding to bone regions whose densities are lower than the average density of the plurality of bone regions, wherein
the display means simultaneously displays the calculated total average and excluded average.

8. A diagnostic imaging support system according to claim 1, further comprising means for calculating, as a total average, an average of characteristic quantities corresponding to a plurality of bone regions of a healthy person, wherein
the display means simultaneously displays the calculated characteristic quantities corresponding to the plurality of bone regions of the healthy person, and the characteristic quantities of the subject.

9. A diagnostic imaging support system, comprising:
input means for setting a characteristic quantity for performing threshold processing for a bone region in an image of a subject;
control means for reading out the image from storage means which stores the image of the subject, extracting a diagnostic region including the bone region from the read image on the basis of the characteristic quantity set by the input means, and calculating, for the extracted diagnostic region, structure analysis information of the bone by use of component identification information representing a bone portion component and a component other than the bone portion; and
display means for displaying the calculated structure analysis information of the bone while relating the structure analysis information to the image of the subject,
wherein the display means displays cross sections of the bone portion of the subject as viewed from a plurality of directions, and displays, on a first cross section, information representing a cut portion of a second cross section, wherein the displayed images of the second cross section correspond to information representing the cut portion selected by a user of the support system.

10. A diagnostic imaging support system according to claim 1, further comprising
means for storing index information of hydroxyapatite measured in advance and contained in the bone portion of the subject,
wherein the display means displays the stored index information of hydroxyapatite and the bone portion of the subject such that the index information and the bone portion are related to each other.

11. A diagnostic imaging support system according to claim 10, further comprising bone-age calculation means for calculating a bone age corresponding to the degree of progress of osteoporosis on the basis of the index information of hydroxyapatite,
wherein the display means displays the degree of progress of osteoporosis by predetermined stepwise-changing numerical levels, while relating it to the calculated bone age.

12. A diagnostic imaging support system according to claim 10, further comprising bone-age calculation means for calculating a bone age corresponding to the degree of progress of osteoporosis on the basis of the index information of hydroxyapatite, wherein the display means displays an index of a treatment policy when the calculated bone age of the subject is older than the actual age.

13. A diagnostic imaging support system according to claim 10, further comprising bone-age calculation means for calculating a bone age corresponding to the degree of progress of osteoporosis on the basis of the index information of hydroxyapatite,
wherein the display means further displays the calculated bone age.

14. A diagnostic imaging support program stored in a non-transitory computer readable medium and including containing a program of instructions executable by a computer to cause the computer to execute the steps of:
(a) reading out an image from a storage unit of the computer;
(b) extracting a diagnostic region including a bone region from the image read in (a), on a basis of a characteristic quantity previously set;
(c) extracting a bone portion component and a component other than the bone portion from the diagnostic region; and (d) calculating structure analysis information of the bone by utilizing at least one of a run length or density of a region that corresponds to the component other than the bone portion.

15. A diagnostic imaging support system comprising:

storage means for storing an image of a subject;

control means for reading out the image from the storage means, extracting a diagnostic region including a bone region from the read image on the basis of a characteristic quantity previously set, extracting a bone portion component and a component other than the bone portion from the extracted diagnostic region, and calculating, for the extracted diagnostic region, structure analysis information of the bone by use of component identification information representing the bone portion component and the component other than the bone portion; and display means for displaying the calculated structure analysis information of the bone for the subject on a graph which shows the relation between age and the calculated structure analysis information of the bone for a plurality of subjects.

\* \* \* \* \*